United States Patent [19]
Yabe et al.

[11] Patent Number: 5,556,367
[45] Date of Patent: Sep. 17, 1996

[54] COVER TYPE ENDOSCOPE APPARATUS

[75] Inventors: Hisao Yabe; Yoshio Tashiro; Yoshihiro IIda; Akira Suzuki; Hideo Itoh; Minoru Yamazaki; Osamu Tamada; Yasuhito Kura, all of Tokyo, Japan

[73] Assignee: Olympus Optical Co., Ltd., Tokyo, Japan

[21] Appl. No.: 38,659

[22] Filed: Mar. 29, 1993

[30] Foreign Application Priority Data

Mar. 5, 1993 [JP] Japan .................................. 5-009178 U
Mar. 5, 1993 [JP] Japan .................................. 5-009179 U
Mar. 5, 1993 [JP] Japan ...................................... 5-045565

[51] Int. Cl.$^6$ ........................................................ A61B 1/04
[52] U.S. Cl. .............................................. 600/124; 600/121
[58] Field of Search ........................... 128/4, 6; 600/121, 600/122, 123, 124, 125

[56] References Cited

U.S. PATENT DOCUMENTS

| | | |
|---|---|---|
| Re. 34,110 | 9/1992 | Opie . |
| 3,162,190 | 12/1964 | Del Gizzo . |
| 4,506,544 | 3/1985 | Shimizu ................................. 73/45.5 |
| 4,646,722 | 3/1987 | Silverstein . |
| 4,721,097 | 1/1988 | D'Amelio . |
| 4,741,326 | 5/1988 | Sidall et al. ................................. 128/4 |
| 4,825,580 | 5/1989 | Opie . |
| 4,869,238 | 9/1989 | Opie . |
| 4,878,485 | 11/1989 | Adair ........................................... 128/6 |
| 4,886,049 | 12/1989 | Darras . |
| 4,907,395 | 3/1990 | Opie . |
| 4,991,564 | 2/1991 | Takahashi . |
| 4,991,565 | 2/1991 | Takahashi . |
| 4,997,084 | 3/1991 | Opie . |
| 5,050,585 | 9/1991 | Takahashi ................................. 128/4 |
| 5,058,567 | 10/1991 | Takahashi . |
| 5,237,984 | 8/1993 | Williams, III et al. ..................... 128/4 |
| 5,257,617 | 11/1993 | Takahashi ................................. 128/4 |

FOREIGN PATENT DOCUMENTS

| | | |
|---|---|---|
| 0184778 | 6/1986 | European Pat. Off. . |
| 0310515 | 4/1989 | European Pat. Off. . |
| 0338567 | 10/1989 | European Pat. Off. . |
| 0341718 | 11/1989 | European Pat. Off. . |
| 0341719 | 11/1989 | European Pat. Off. . |
| 0349479 | 1/1990 | European Pat. Off. . |
| 0440252 | 8/1991 | European Pat. Off. . |
| 0440254 | 8/1991 | European Pat. Off. . |
| 0444429 | 9/1991 | European Pat. Off. . |
| 3909290 | 10/1989 | Germany . |
| 51-47587 | 4/1976 | Japan . |
| 51-103891 | 8/1976 | Japan . |
| 52-95284 | 7/1977 | Japan . |
| 58-44033 | 3/1983 | Japan . |
| 62-177701 | 11/1987 | Japan . |
| 1-140902 | 9/1989 | Japan . |
| 2-57228 | 2/1990 | Japan . |
| 2-54734 | 11/1990 | Japan . |
| 3-29634 | 2/1991 | Japan . |
| 3-29635 | 2/1991 | Japan . |
| 3-37029 | 2/1991 | Japan . |
| 3-13105 | 2/1991 | Japan . |
| 3-37030 | 2/1991 | Japan . |
| 3-221024 | 9/1991 | Japan . |
| 3-101903 | 10/1991 | Japan . |
| 3-101904 | 10/1991 | Japan . |
| 3-101905 | 10/1991 | Japan . |
| 3-101906 | 10/1991 | Japan . |
| 3-101907 | 10/1991 | Japan . |
| 3-101901 | 10/1991 | Japan . |
| 3-101902 | 10/1991 | Japan . |
| H4-325138 | 11/1992 | Japan . |

*Primary Examiner*—Richard J. Apley
*Assistant Examiner*—Beverly M. Flanagan
*Attorney, Agent, or Firm*—Armstrong, Westerman, Hattori, McLeland & Naughton

[57] ABSTRACT

A cover type endoscope apparatus including an endoscope cover and an endoscope to be covered which is used by being inserted into the endoscope cover. The endoscope cover can be used in common for covering a plurality of endoscopes to be covered having different lengths without changing the length of the cover.

5 Claims, 22 Drawing Sheets

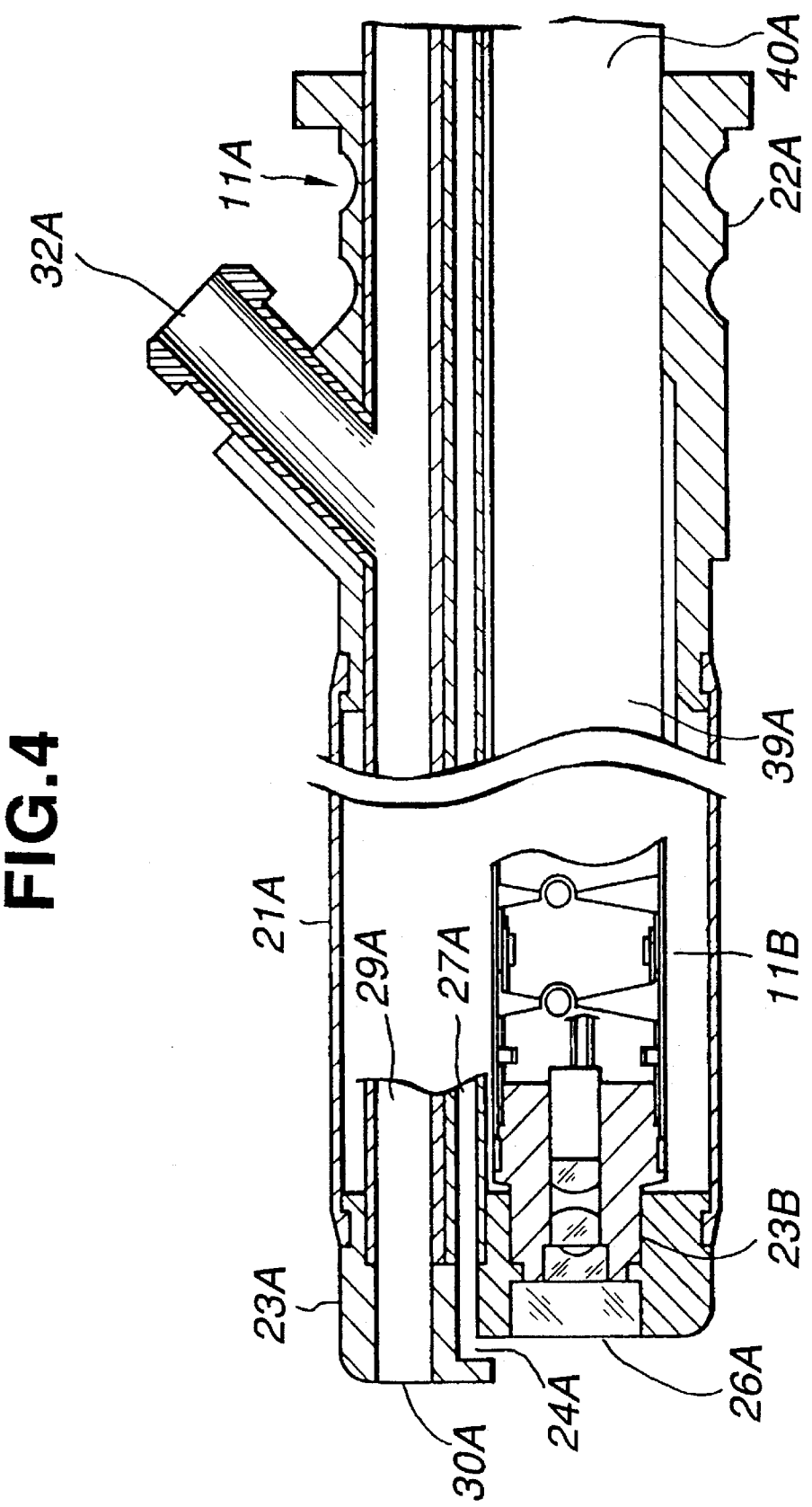

COVER TYPE ENDOSCOPE APPARATUS

BACKGROUND OF THE INVENTION

1. Field of the Invention

The present invention relates to an endoscope cover type endoscope apparatus which uses an endoscope to be covered by inserting the endoscope to be covered into an endoscope cover.

2. Description of the Related Art

Recently, endoscopes have been widely used in the field of medical treatment. When an endoscope used in the field of medical treatment is inserted into a living body, an observation window provided at the tip of an-insertion tube is sometimes soiled by bodily fluid, so that the endoscope cannot clearly observe the inside of the living body. Therefore, an endoscope is provided with air supplying and water supplying functions so as to be able to wash the observation window by spraying the observation window with water and to blow excess water off by supplying air from the proximal portion of the endoscope. Further, the supplying air function can also be used in a case in which air is supplied to the body cavity to observe an observation portion easily. The air and water are supplied through an air supplying channel and water supplying channel.

Further, the endoscope is provided with a forceps channel (treatment tool channel) so as to be able to collect tissues by means of biopsy forceps or to be able to give treatment using treatment tools.

In an endoscope used in such a medical treatment field, an endoscope used once for a patient is washed or disinfected to prevent infection. However, it takes time to wash and disinfect it completely. Thus, the maneuverability of the endoscope is low and also, use efficiency of the endoscope is lowered.

Especially, each of the aforesaid channels was connected to the outside of a living body through a channel from a tip opening portion which opened into the body cavity of a patient, so that it was troublesome to completely wash and disinfect the tip opening portion and the inside of the channel.

Therefore, recently, what is known as a cover type endoscope has been adopted. In the cover type endoscope, an endoscope itself is covered with an endoscope cover and the endoscope cover is thrown away in each and every treatment to simplify the washing and disinfection after use.

By use of the cover type endoscope, even in an expensive video endoscope using illumination means and a solid state imaging device (SID), a channel which opens into the body cavity of a patient is provided in the aforesaid endoscope cover so that the observation means and illumination means which do not open into the body cavity are provided in the endoscope, and are covered with an endoscope cover. Thus, the video endoscope does not become unclean after use and also, washing and disinfecting can be simplified by throwing the endoscope cover away.

Such a cover type endoscope is disclosed, for example, in U.S. Pat. No. 4,646,722 and No. 3,162,190.

As shown in FIG. 1, in such a cover type endoscope, a catching groove 103 is formed on the inner periphery of a connector for fixing endoscope operation part 102 provided on the upper portion of an endoscope cover 101 and an engaging portion 105 engaged with the catching groove 103 is formed on the outer periphery of an endoscope to be covered 104 to be inserted into the catching groove 103. Therefore, the endoscope cover 101 is fixed on the endoscope to be covered 104.

The length of the insertion tube 104a of the aforesaid endoscope to be covered 104 is determined in every purpose and affected part to be used. If the length of the insertion tube 104 changes, the endoscope cover 101 for covering should be selected in accordance with the endoscope to be covered 104 which is used, as well.

That is, when the length of an insertion tube 104a of the endoscope to be covered 104 is shorter than the length of an insertion tube 101a of the endoscope cover 101, an opening is made between the tip of the insertion tube 104a and the tip of the insertion tube 101a of the endoscope cover 101. Thus, a close-up area cannot be observed. Then, illuminating light is reflected in a cover lens of the endoscope cover 101 and enters an observation optical system and then causes inconvenient optical effects, such as flare.

On the other hand, if the length of the insertion tube 104a of the endoscope to be covered 104 is longer than the length of the insertion tube 101a of the endoscope cover 101, the catching groove 103 of the endoscope 101 will not be engaged with the engaging portion 105 of the endoscope to be covered 104, so that the endoscope cover 101 cannot be fixed to the endoscope to be covered 104.

Therefore, the endoscope cover 101 applied to the endoscope to be covered 104 had to be selected conventionally. Not only the preparatory operation takes time but also many kinds of endoscope covers 101 should be previously prepared. Thus, the preparation was time-consuming.

In addition, even for the same purpose, it is technically difficult to produce the endoscope to be covered 104 and endoscope cover 101 having the same length. The aforesaid problem is also made by an uneven common difference between the endoscope to be covered 104 and endoscope cover 101 which are used for the same purpose.

The operation for fitting the endoscope cover to the endoscope to be covered is sometimes performed on an endoscope cover tray which is kept clean. Such an endoscope to be covered has a structure in which an insertion tube to be inserted into the body cavity, and a connecting cord portion having a connector connected to external devices such as a light source and video processor are arranged in an L shape and the connecting cord portion does not become an obstacle when the endoscope is operated at an operation part provided in a proximal portion of the aforesaid insertion tube.

However, if the aforesaid insertion tube and connecting cord portion are arranged in an L shape, the endoscope cover fitted to the endoscope to be covered should be subdivided into the insertion tube, operation part and connecting cord portion of the endoscope to be covered, respectively. Therefore, it is troublesome to fit the cover to them and maneuverability is low.

If the aforesaid endoscope to be covered is formed in an L shape, a shape of an endoscope cover tray which is used when the endoscope to be covered is fitted to the endoscope cover should be an L shape. Since the formation of an L shaped tray for an endoscope cover makes the volumetric efficiency of the tray worse, there is a problem in housing capacity and handling capacity.

Further, as mentioned above, an endoscope used as the endoscope of a cover type (temporally called as "endoscope to be covered") is not provided with sucking channel, supplying air channel and supplying water channel. Each of these channels is provided in an endoscope cover and exchanged in every treatment.

Accordingly, the shape of the external connecting portion of the endoscope to be covered can be smaller and lighter than the outer connecting portion of a general coverless endoscope by the portion in which the aforesaid channels are not provided.

If the external connecting portion of an endoscope to be covered becomes smaller and lighter, an endoscope to be covered can be easily handled. Additionally, an external device, such as a light source device for connecting the external connecting portion can be smaller.

However, if the shape of the external connecting portion is different from that of a general coverless endoscope, the interchangeability for a controlling device such as a light source and video processor which are the external devices of the coverless endoscope is lost, so that a user has to equip the aforesaid external devices when the endoscope to be covered is used and that the user is forced to pay the expense of the equipment.

SUMMARY OF THE INVENTION

An object of the present invention is to provide a cover type endoscope apparatus which can handle many kinds of endoscopes to be covered having different lengths and uneven common difference by one endoscope cover, which can make endoscope preparatory operation short and can reduce the number of the kinds of endoscope covers so that the cover type endoscope can be easily controlled.

Another object of the present invention is to provide a cover type endoscope apparatus which can connect an external connecting portion of an endoscope to be covered to an external device of a coverless endoscope apparatus and which can be easily handled and is also economical.

Further, another object of the present invention is to provide a cover type endoscope apparatus in which an endoscope cover does not need to be subdivided; a fitting operation to an endoscope to be covered is easily performed; a shape of an endoscope cover tray can be formed as a shape having good volumetric efficiency and the endoscope cover tray is easily housed and handled.

A cover type endoscope apparatus of the present invention comprises an endoscope cover and an endoscope to be covered which is used by being inserted into the endoscope cover. The aforesaid endoscope cover can be used in common for covering a plurality of endoscopes to be covered having different lengths.

These objects and advantages of the present invention will be further apparent from the following explanation.

BRIEF DESCRIPTION OF THE DRAWINGS

FIGS. 1 to 4 show the first embodiment of the present invention.

FIG. 2 is a general schematic view of a cover type endoscope apparatus.

FIG. 4 is a cross-sectional view of an insertion tube of an endoscope to be covered.

FIG. 16 is a schematic view of the essential part of a cover type endoscope apparatus.

FIG. 17 is a side view of a connector on a cover type endoscope side.

FIG. 18 is a perspective view of an adapter body.

FIG. 19 is a sectional view of a cover type endoscope side connector as connected to a light source device through the adapter body.

FIG. 20 is a wiring diagram of the essential part of a cover type endoscope apparatus.

FIG. 24 is a perspective view of an adapter body.

FIG. 25 is a vertically sectioned view of FIG. 24.

FIG. 26 is a wiring diagram of the essential part of a cover type endoscope apparatus.

FIG. 27 is a sectional view of a related cover type endoscope tip portion.

FIG. 28 is a sectional view of a cover type endoscope tip portion.

FIG. 30 is an exploded view of a cover type endoscope.

FIG. 31 is a perspective view of an endoscope cover tray.

FIG. 32 is an exploded view of a cover type endoscope.

FIG. 33 is a sectional view of the essential part of a cover type endoscope.

FIGS. 34 to 36 show the 22nd embodiment of the present invention.

FIG. 34 is a perspective view of a cover package housing an endoscope cover.

FIG. 35 is a perspective view of a cover package as a second housing case is opened.

FIG. 40 is a sectional view of a packaging case.

FIG. 41 is a sectional view of a packaging case as opened.

FIG. 44 is a perspective view of an endoscope cover tray.

FIG. 45 is a sectional view of the essential part of FIG. 44.

FIG. 50 is a perspective view of an endoscope cover tray.

FIG. 51 is a sectional view of an endoscope cover tray.

DETAILED DESCRIPTION OF THE PREFERRED EMBODIMENTS

Figure 1:
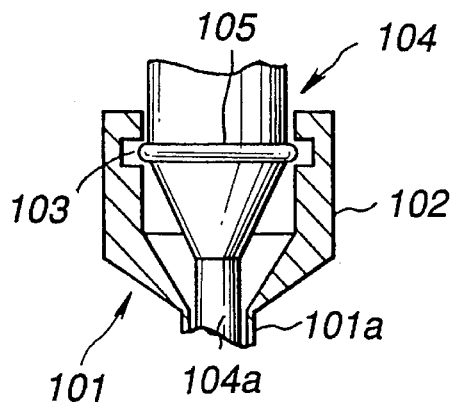
FIG. 1 is a sectional view of the essential part of a conventional endoscope to be covered as fitted to an endoscope cover.
Figure 2:
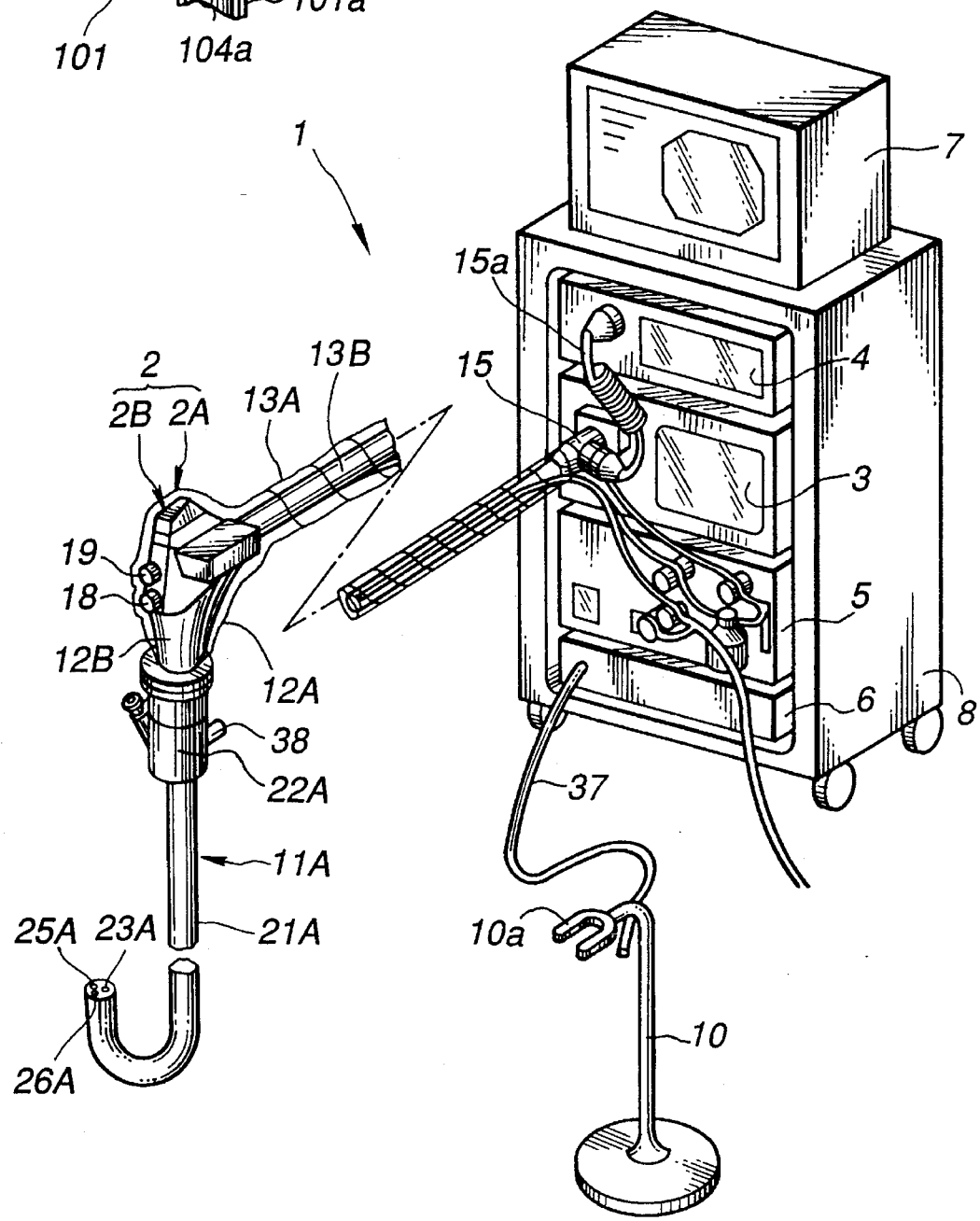

FIGS. 2 to 4 show the first embodiment of the present invention.

As shown in FIG. 2, a cover type endoscope apparatus 1 comprises a channeled endoscope cover type endoscope (which shall be hereinafter briefly mentioned as the "cover type endoscope") comprising a channeled endoscope cover (which shall be hereinafter briefly mentioned as the "endoscope cover") 2A and an endoscope to be covered with the channeled endoscope cover (which shall be hereinafter briefly mentioned as the "endoscope to be covered") 2B to be fitted to the endoscope cover 2A, a light source device 3 feeding illuminating light to the endoscope to be covered 2B, a video processor 4 processing signals for imaging means built-in in the endoscope to be covered 2B, a fluid controlling device 5 for supplying air and water through tubes of the endoscope cover 2A, a channeled endoscope cover expander (which shall be hereinafter briefly mentioned as the "expander") 6 and a monitor 7 for displaying video signals processed by the aforesaid video processor 4. The light source device 3, video processor 4, fluid controlling device 5 and expander 6 are housed in a cart 8 and the monitor 7 is mounted on the upper surface of the cart 8.

In the case of an endoscope examination, the clean endoscope to be covered 2B is covered with the clean endoscope cover 2A and, after the examination, the endoscope cover 2A is abandoned. On the other hand, the endoscope to be covered 2B is covered with a new clean endoscope cover 2A and is repeatedly used.

In a case in which the endoscope to be covered 2B is to be fitted to an insertion tube cover portion 11A forming the endoscope cover 2A, a cover holder 10 shown in FIG. 2 is used. For example, the proximal end side of an insertion tube cover portion 11A is hung on a cover holding member 10a and an endoscope insertion tube 11B of the endoscope to be covered 2B is fitted.

The aforesaid endoscope to be covered 2B comprises a long, narrow, flexible endoscope insertion tube (which shall be hereinafter briefly mentioned as an "insertion tube") 11B, an endoscope operation part (which shall be hereinafter briefly mentioned as the "operation part") 12B and a universal cord 13B extending out of the side of the operation part 12B. An illumination optical system and an observation optical system making the aforesaid imaging means form an object image are arranged at the tip of the aforesaid insertion tube 11B. When a connector 15 provided at the distal end of the aforesaid universal cord 13B, illuminating light from a lamp within the aforesaid light source device 3 is fed to the aforesaid illumination optical system through a light guide (not illustrated) inserted through the aforesaid universal cord 13B and insertion tube 11B.

The illuminating light fed to the illumination optical system is emitted to the forward object side through a transparent plate of a cover illumination window 25A provided on the end surface of a cover tip portion 23A of the aforesaid insertion tube cover portion 11A provided opposite the illumination window (not illustrated) of the tip portion 23B of the insertion tube 11B.

Such illumination object as an affected part forms an optical image on an imaging surface of such imaging means as a solid state imaging device (SID) arranged in a focal plane through a transparent plate of a cover observation window 26A provided adjacent to a cover illumination window 25A and an observation optical system provided in the insertion tube 11B of the endoscope 2B to be covered arranged inside the cover observation window 26A as opposed to it.

The optical image formed on the imaging surface is photoelectrically converted, is input into the video processor 4 through a signal cable 15a inserted through the insertion tube 11B and universal cord 13B and is processed to be a signal and then a standard video signal is produced and is input into the monitor 7 and an object image is displayed on a displaying screen.

The aforesaid operation part 12B and endoscope to be covered 2B are provided with an air and water (or only water) supplying switch 18, sucking switch 19, image switching switch 20 and bending operation knob (not illustrated) so that, by operating the switches and knobs, air and water may be supplied or sucked (or only water may be supplied), images may be switched so as to be frozen or released and a bent angle of the tip bending part provided in the insertion tube 11B are set.

On the other hand, the endoscope cover 2A comprises an insertion tube cover portion 11A, operation part cover 12A and universal cord cover 13A covering the insertion tube 11B, operation part 12B and universal cord 13B of the endoscope to be covered 2B, respectively.

The insertion tube cover portion 11A comprises an insertion tube cover outer cover 21A covering the insertion tube 11B, connector for fixing an endoscope operation part 22A provided airtightly at the proximal end of the insertion tube cover outer cover 21A and a cover tip portion 23A provided airtightly at the distal end of the insertion tube cover outer cover 21A.

Within the insertion tube cover portion 11A are formed an air and water supplying channel 27A and sucking channel 29A and an endoscope insertion channel 39A for inserting (fitting) the insertion tube 11B of the aforesaid endoscope to be covered 2B. The aforesaid air and water supplying channel 27A is made to communicate with a nozzle 24A provided on the end surface of the cover tip portion 23A and the tip opening of the nozzle 24A is opposed to the outer surface of the cover observation window 26A.

The proximal ends of the aforesaid air and water supplying channel 27A and sucking channel 29A are extended out above a connector for fixing the endoscope operation part 22A and are extended out on the fluid controlling device 5 side as covered with the universal cord cover 13A together with the universal cord 13B. A water supplying channel 28A is connected to a water supplying tank 30. The air and water supplying channel 27A is made to communicate with an air supplying pump 31 and is branched in the course to be the upper direction of the aforesaid water supplying tank 30. Further, the sucking channel 29A is made to communicate with a suction pump (not illustrated). A forceps outlet 30A communicating with the aforesaid sucking channel 29A is opened in the aforesaid cover tip portion 23A. Further, a forceps insertion port 32A communicating with the aforesaid sucking channel 29A is provided in the connector 22 for fixing the aforesaid endoscope operation part.

Also, an expanding tube connector 38 connecting an expanding tube 37 connected to the expander 6 is provided on the side of the connector for fixing the endoscope operation part 22A.

Further, an opening portion 40A of the aforesaid endoscope insertion channel 39A is provided on the upper surface of the connector 22A for fixing the endoscope operation part.

The aforesaid expander 6 usually continues to supply air. Therefore, when the function of the expander 6 is not used, as shown in FIG. 2, the distal end of the expanding tube 37 is not connected with the expanding tube connector 38 and communicates with the outside atmosphere. When the endoscope to be covered 2B is to be inserted into the insertion tube cover portion 11A, by the operation of pushing the distal end of the expanding tube 37 into the expanding tube connector 38, the endoscope is airtightly inserted (fitted) and connected, air supplied from the expander 6 is supplied into the endoscope insertion channel 39A through the expanding tube connector 38 to inflate the endoscope insertion channel 39A and it is easy to insert the insertion tube 11B.

Figure 3A:
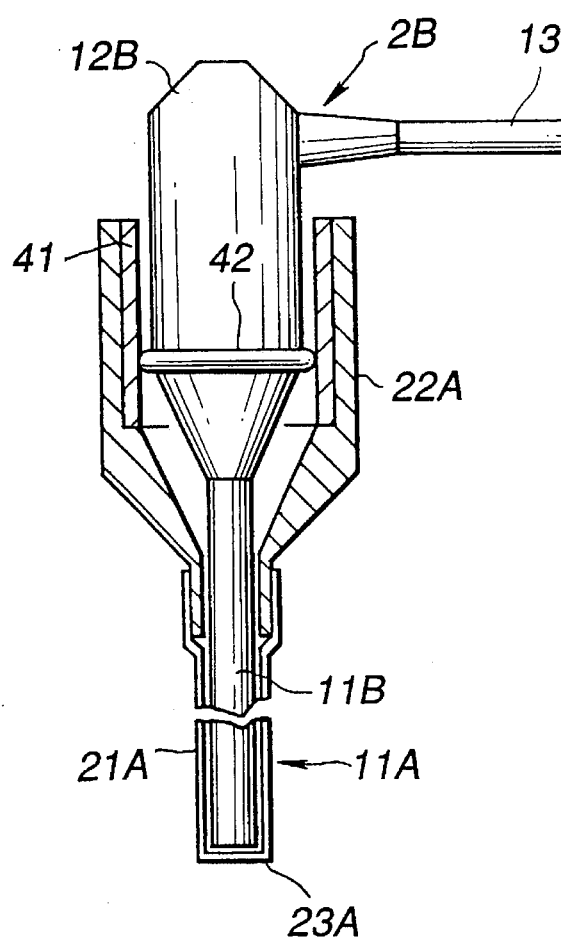
FIGS. 3(a) and 3(b) are sectional views of an endoscope to be covered of a different length as fitted to an endoscope cover.
Figure 3B:
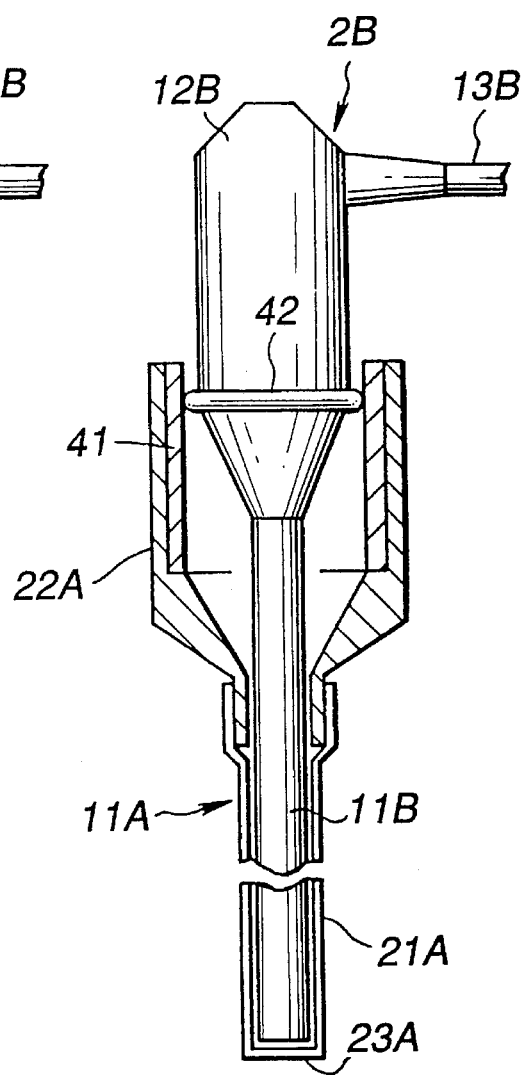

As shown in FIGS. 3(a) and 3(b), a fitting portion 41 made of an elastic material as length adjusting means is provided on the inner periphery of the endoscope operation part fixing connector 22A provided on the proximal side of the aforesaid insertion tube cover portion 11A. An engaging portion 42 closely fitting the fitting portion 41 is provided in the position corresponding to the aforesaid fitting portion 41 of the aforesaid endoscope to be covered 2B. The fitting portion 41 is continuously provided toward the tip from the opening end of the connector for fixing the aforesaid endoscope operation part 22A.

The operation of the aforesaid embodiment shall be explained in the following.

First, in a case in which the endoscope to be covered 2B is to be inserted (fitted) into the insertion tube cover portion 11A of the endoscope cover 2A, the connector for fixing the endoscope operation part 22A is held with a semicircular cover holding member 10a provided in the holder 10.

When the distal end of the expanding tube 37 is then connected to the expanding tube connector 38 and the tip of the insertion tube 11B of the endoscope to be covered 2B is inserted into the endoscope insertion channel 39A from the opening portion 40A, the opening portion 40A will be narrowed by the aforesaid insertion tube 11B, air will be supplied into the aforesaid endoscope insertion channel 39A and the endoscope insertion channel 39A will be inflated.

The tip of the aforesaid insertion tube 11B is inserted to contact the cover observation window 26A provided at the tip.

At this time, the engaging portion 42 provided on the aforesaid endoscope to be covered 2B slides to be positioned in the fitting portion 41 provided on the inner periphery of the connector for fixing the endoscope operation part 22A of the aforesaid endoscope insertion tube cover portion 11A and is fixed as closely fitted by friction.

As a result, as shown in FIG. 3(a), when the endoscope to be covered 2B having a short insertion tube 11B is fitted to the aforesaid insertion tube cover portion 11A, the engaging portion 42 of the endoscope to be covered 2B is engaged in the inner position of the connector for fixing the endoscope operation part 22A of the aforesaid insertion tube cover portion 11A. Also, as shown in FIG. 3(b), the endoscope to be covered 2B having a long insertion tube 11B is fitted to the aforesaid insertion tube cover portion 11A, the engaging portion 42 of the endoscope to be covered 2B is fitted and fixed on the opening end of the connector for fixing the endoscope operation part 22A.

Thus, the common insertion tube cover portion 11A can steplessly correspond to a plurality of the endoscopes to be covered 2B having different length insertion tubes 11B and is therefore economical. Also, the aforesaid fitting portion 41 can cope with the uneven common difference between the insertion tube cover portion 11A and the aforesaid endoscope to be covered 2B.

By providing a plurality of the engaging portions 42 in the aforesaid endoscope to be covered 2B, the aforesaid insertion tube cover portion 11A can be securely held and fixed by the aforesaid endoscope to be covered 2B.

After the inserting operation ends, when the distal end of the expanding tube 37 is removed from the expanding tube connector 38, the aforesaid endoscope insertion channel 39A shrinks by its elasticity (the outside diameter of the insertion tube cover outer cover 21A becomes smaller) and the outer surface of the insertion tube 11B, that is, the outer cover of the insertion tube 11B substantially closely fits its inner surface.

Then, the operation part 12B of the aforesaid endoscope 2B to be covered is covered with the operation part cover 12A, and its opening end is closely fitted to the upper end of the connector for fixing the endoscope operation part 22A of the aforesaid insertion tube cover portion 11A, the universal cord 13B is covered with the universal cord cover 13A and the aforesaid endoscope 2B to be covered is sealed and inspected.

Figure 5:
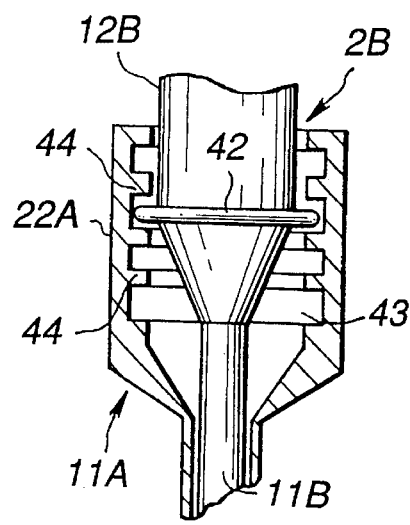
FIG. 5 is a sectional view of the essential part of an endoscope to be covered in the second embodiment of the present invention as fitted to an endoscope cover.

FIG. 5 shows the second embodiment of the present invention.

In this embodiment, a plurality of steps of engaging grooves 43 engaging the engaging portion 42 of the endoscope to be covered 2B are annularly provided as length adjusting means on the inner periphery of the connector for fixing the endoscope operation part 22A of the insertion tube cover portion 11A so that the aforesaid engaging part 42 may be engaged with these engaging grooves 43 with a favorable moderation sense.

The portion between the aforesaid engaging grooves 43 formed on the inner periphery of the connector for fixing the aforesaid endoscope operation part 22A is formed of an elastically transformable sliding portion 44 so that, when the aforesaid endoscope 2B to be covered is slid, these sliding portions are elastically transformed to pass the aforesaid engaging portion 42.

Figure 6:
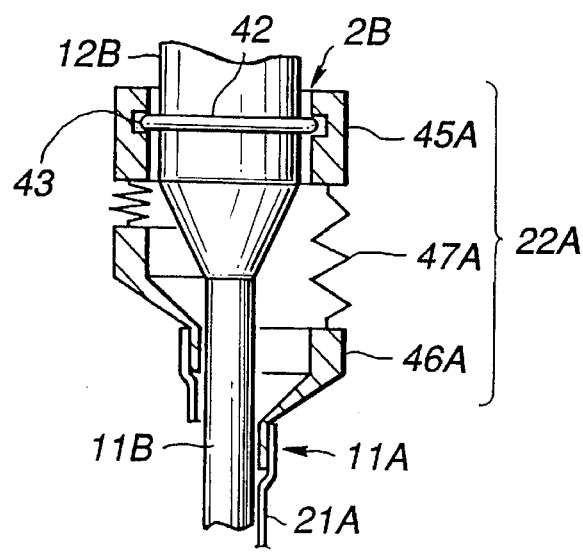
FIG. 6 is a sectional view of the essential part of an endoscope to be covered in the third embodiment of the present invention as fitted to an endoscope cover.

FIG. 6 shows the third embodiment of the present invention.

In this embodiment, the connector for fixing the endoscope operation part 22A of the insertion tube cover portion 11A compromises a first connector 45A on the opening end, a second connector 46A connected on the insertion tube cover outer cover 21 and an extending and contracting portion 47A consisting of an accordion-type tube as length adjusting means connecting both connectors 45A and 46A with each other. When the endoscope to be covered 2B is inserted into the insertion tube cover portion 11A from the connector for fixing the endoscope operation part 22A, the insertion tube tip of the aforesaid endoscope to be covered 2B contacts the inner surface of the tip of the aforesaid insertion tube cover portion 11A, the insertion tube cover outer cover 21A of the insertion tube cover portion 11A is pulled and the aforesaid extending and contracting portion 47A extend and relatively inserts the endoscope to be covered 2B into the insertion tube cover portion 11A until the engaging portion 42 provided on the endoscope to be covered 2B is caught in the engaging groove 43 annularly provided on the inner periphery of the first connector 45A.

As a result, one insertion tube cover portion 11A can be used in common for a plurality of kinds of endoscopes to be covered 2B having different length insertion tubes 11B.

Figure 7:
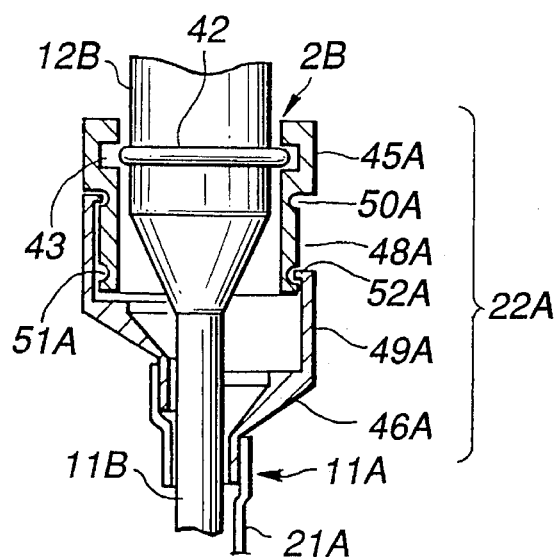
FIG. 7 is a sectional view of the essential part of an endoscope to be covered in the fourth embodiment of the present invention as fitted to an endoscope cover.

FIG. 7 shows the fourth embodiment of the present invention.

In this embodiment, the first connector 45A and second connector 46A of the connector for fixing the endoscope operation part 22A shown in the aforesaid third embodiment are integrally provided with sliding portions 48A and 49A which are length adjusting means overlappable on each other. A first engaging groove 50A is annularly provided on the proximal portion of the sliding portion 48A on the first connector 45A side and a second engaging groove 51A is annularly provided on the tip side of the sliding portion 48A.

On the other hand, a rib 52A engaging selectively with the aforesaid engaging grooves 50A and 51A is annularly provided at the upper end of the aforesaid sliding portion 49A on the second connector 46A side. The engaging portion comprises these engaging grooves 50A and 50B and the aforesaid rib 52A.

As shown on the left side in FIG. 7, in a case in which the length of the insertion tube 11B of the endoscope to be covered 2B is short, when the rib 52A provided on the sliding portion 49A on the aforesaid second connector 46A side is engaged with the first engaging groove 50A provided in the aforesaid first connector 45A, the entire length of the insertion tube cover portion 11A covering the insertion tube 11b of the aforesaid endoscope to be covered 2B becomes short and, when the aforesaid rib 52A is engaged with the aforesaid second engaging groove 51A, the length of the aforesaid insertion tube cover portion 11A becomes long. As a result, one endoscope cover 11A can correspond to the endoscopes to be covered 2B and of two different lengths.

Figure 8:
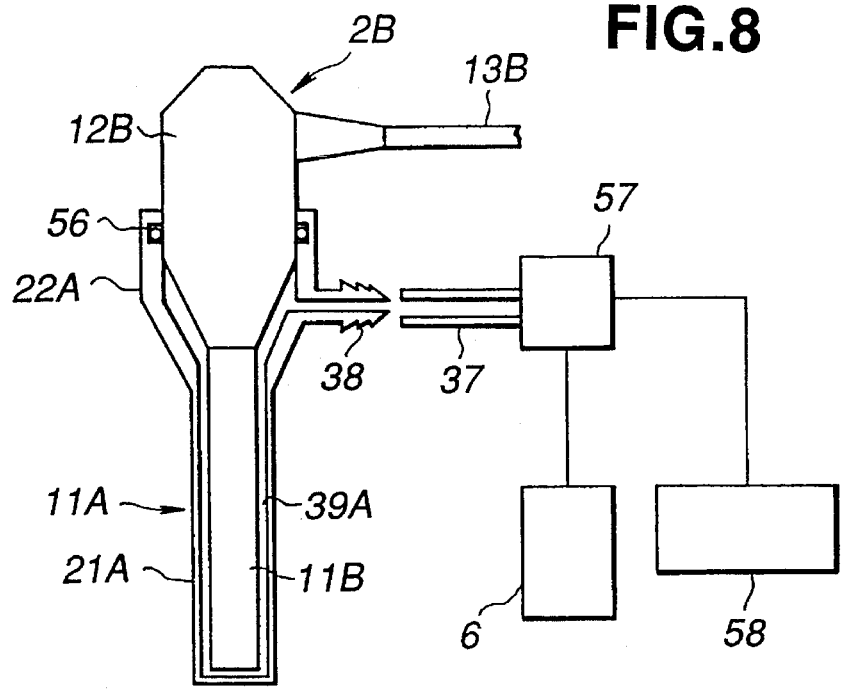
FIG. 8 is a schematic view of the essential part of a cover type endoscope apparatus in the fifth embodiment of the present invention.

FIG. 8 shows the fifth embodiment of the present invention.

As shown in this embodiment, when a switching portion 57 is interposed between the expander 6 and expanding tube 37 and an airtightness detecting device 58 is made to communicate with the switching portion 57, such damaged portion as a pinhole of the endoscope insertion channel 39A of the insertion tube cover portion 11A can be detected by the airtightness detecting device 58.

That is to say, an interval between the insertion tube cover portion 11A and the endoscope to be covered 2B inserted into the insertion tube cover portion 11A is fixed with a sealing member 56 made of an elastic material, such as rubber, which is an example of an airtight means provided at the opening end of the endoscope operation part fixing connector 22A of the aforesaid insertion tube cover portion 11A and the interior is kept airtight.

When the endoscope to be covered 2B is fitted to the insertion tube cover portion 11A, the expanding tube 37 extended out of the aforesaid switching portion 57 is connected to an expanding tube connector 38 provided on the insertion tube cover portion 11A and air is supplied into the aforesaid insertion tube cover portion from the aforesaid expander 6 selected in the switching portion 57 to inflate the insertion tube cover portion 11A to which the aforesaid endoscope to be covered 2B is fitted.

Thereafter, when it is confirmed that the aforesaid insertion tube cover portion 11A is fixed to the aforesaid endoscope to be covered 2B, in the aforesaid switching portion 57, the aforesaid airtightness detecting device 58 is made to communicate with the aforesaid expanding tube 37. In the airtightness detecting device 58, air is once supplied into the aforesaid endoscope insertion channel 39A to pressurize the endoscope insertion channel 39A. Then, the pressure fluctuation within the endoscope insertion channel 39A is sensed to confirm whether or not the airtightness is held.

When the airtightness is confirmed to be held, the insertion tube cover portion 11A is usable and therefore the expanding tube 37 is removed from the aforesaid expanding tube connector 38, so that the aforesaid insertion tube cover portion 11A shrinks with its self-elastic force and the endoscope insertion channel 39A is closely fitted to the outer cover of the insertion tube 11B of the aforesaid endoscope to be covered 2B.

On the other hand, in a case in which the airtightness within the aforesaid endoscope insertion channel 39A is imperfect, the insertion tube cover portion 11A is likely to have broken and is replaced.

Thus, when the endoscope insertion tube 11A and the aforesaid endoscope to be covered 2B are not airtight when fitted, it is troublesome to detect a broken part. However, as in this embodiment, when the interval between the insertion tube cover portion 11A and the aforesaid endoscope to be covered 2B and inserted into this insertion tube cover portion 11A is sealed with a sealing member 56, the broken state will be able to be easily confirmed.

Figure 9:
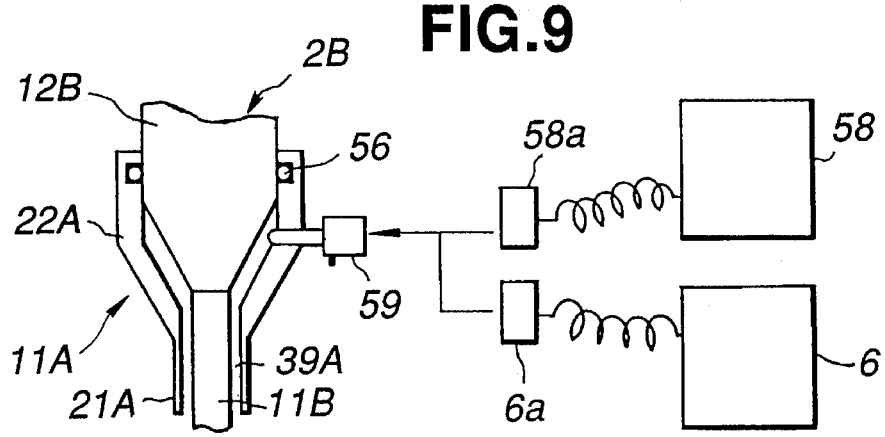
FIG. 9 is a schematic view of the essential part of a cover type endoscope apparatus in the sixth embodiment of the present invention.

FIG. 9 shows the sixth embodiment of the present invention.

In this embodiment, instead of an expanding tube connector 38, an air supplying connector 59 used on a coverless endoscope is provided for the connector for fixing the endoscope operating part 22A of the aforesaid insertion tube cover portion 11A, and connectors 58a and 6a connectable to the aforesaid air supplying connector 59 are provided for the airtightness detecting device 58 and expander 6, respectively. The aforesaid air supplying connector 59 is made to communicate only when either of the aforesaid connectors 58a and 6a is connected.

According to this embodiment, after the expander 6 side connector 6a is fitted to the aforesaid air supplying connector 59, even if the airtightness detecting device 58, side connector 58a, is fitted to the air supplying connector 59, the airtightness within the aforesaid endoscope insertion channel 39A is held. Because the air supplying connector 59 is in common with the one used in the coverless endoscope, the air supplying device and the airtightness detecting device of the coverless endoscope can be connected to the air supplying connector 59 to be high in general usability.

Figure 10:
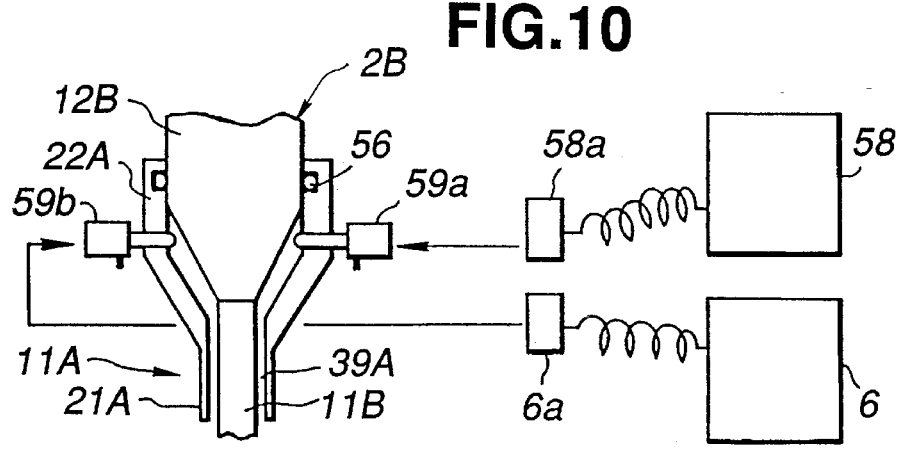
FIG. 10 is a schematic view of the essential part of a cover type endoscope apparatus in the seventh embodiment of the present invention.

FIG. 10 shows the seventh embodiment of the present invention.

As shown in this embodiment, an air supplying connector for the airtightness detecting device 59a and an air supplying connector for the expander 59b may be separately provided on the connector for fixing the aforesaid endoscope operation part 22A.

Figure 11:
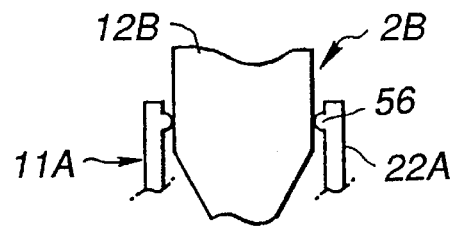
FIG. 11 is a schematic view of the essential parts of the operation part and insertion tube cover portion of a cover type endoscope apparatus in the eighth embodiment of the present invention.

FIG. 11 shows the eighth embodiment of the present invention.

As shown in this embodiment, the aforesaid sealing member 56 may be provided integrally with the insertion tube cover portion 11A.

Figure 12:
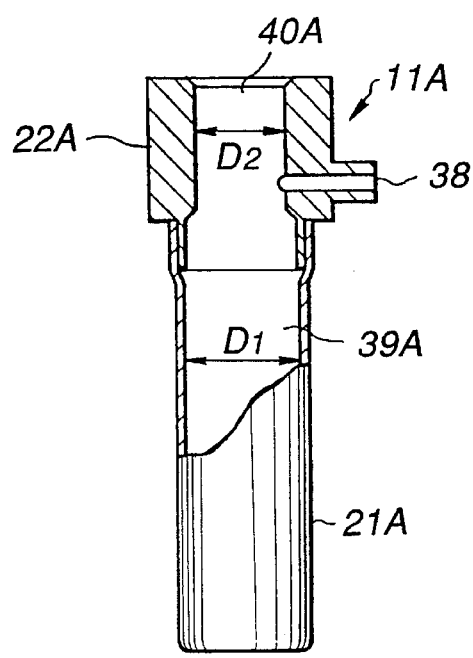
FIG. 12 is a partial sectional side view of an insertion tube cover portion in the ninth embodiment of the present invention.

FIG. 12 shows the ninth embodiment of the present invention.

As shown in this embodiment, the inside diameter D1 of the endoscope insertion channel 39A of the insertion tube cover portion 11A and the inside diameter D2 of the opening portion 40A of the aforesaid endoscope insertion channel 39A formed in the connector for fixing the endoscope operation part 22A are made D1>D2 so that, when the endoscope to be covered is inserted into the aforesaid endoscope insertion channel 39, the force applied to a thick opening portion 40A increases, the force applied to a thin outer cover of the insertion tube cover 21A is attenuated a great deal and, as a result, the outer cover 21A of the insertion tube cover can be prevented from being damaged.

On the other hand, as a related art, the range from the aforesaid opening 40A to the aforesaid endoscope insertion channel 39A is set to be substantially of the same diameter. However, therein, when the insertion tube of the endoscope to be covered is to be inserted into the insertion tube cover portion 11A, it has to be inserted with care so as not to be damaged.

Figure 13:
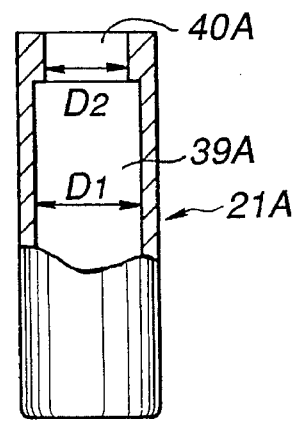
FIG. 13 is a partial sectional side view of an insertion tube cover portion in the tenth embodiment of the present invention.

FIG. 13 shows the tenth embodiment of the present invention.

Even in such a type as is shown in this embodiment wherein, in the insertion tube cover portion 21A having no connector for fixing the endoscope operation part 22A, only the insertion tube of the endoscope to be covered is covered. If the opening portion 40A of the insertion tube cover portion 21A is formed to be thick and the inside diameter D1 of the endoscope insertion channel 39A and the inside diameter D2 of the opening portion 40A are made to be D1>D2, the same effects as described above are obtained.

Figure 14:
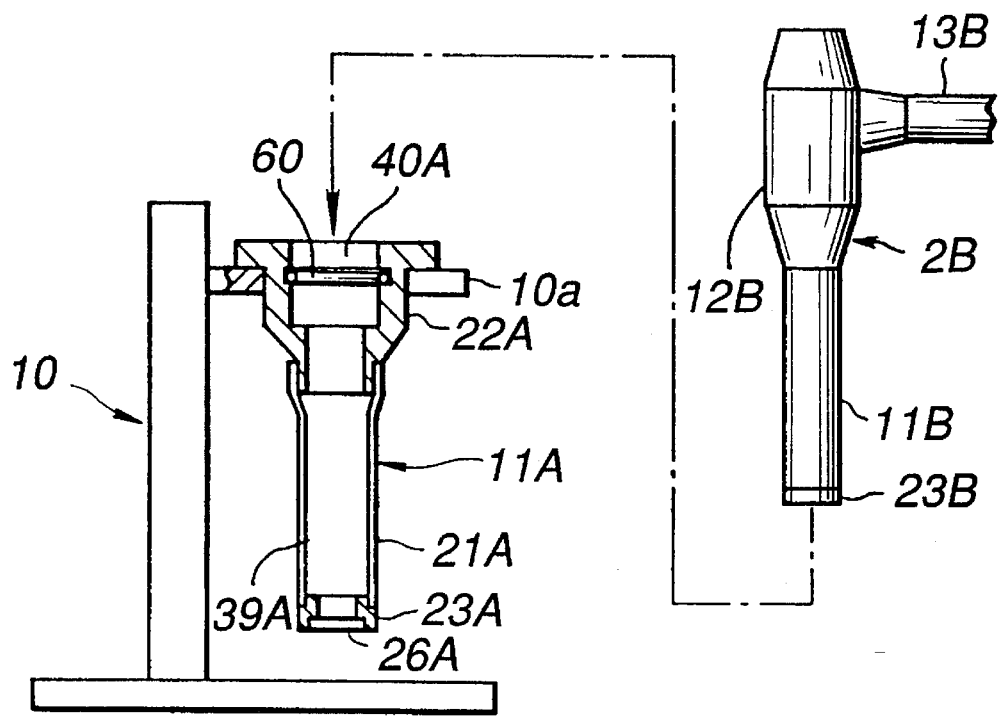
FIG. 14 is a schematic view showing an endoscope cover and an endoscope to be covered as fitted to each other in the 11th embodiment of the present invention.

FIG. 14 shows the 11th embodiment of the present invention.

As shown in this embodiment, if a fitting portion 60 made of such elastic material as rubber is annularly provided on the inner periphery of the opening portion 40A formed in the connector for fixing the endoscope operation part 22A of the endoscope cover portion 11A, the fitting portion 60 fits the operation part 12B of the endoscope to be covered 2B and the insertion tube cover portion 11A can be fixed to the endoscope to be covered 2B. At this time, the tip portion 23B of the insertion tube 11B of the endoscope to be covered 2B is in contact with the tip surface on the inner surface of the cover tip portion 23A of the insertion tube cover portion 11A.

As a related art, the tip portion 23B of the insertion tube 11B of the endoscope to be covered 2B is fitted to the inner peripheral surface of the cover tip portion 23A of the insertion tube cover portion 11A to fix the aforesaid endoscope cover 11A to the aforesaid endoscope to be covered 2B. However, in order to carry out the covering operation without contaminating the insertion tube cover portion 11A, as described above, the endoscope insertion tube 11B of the endoscope to be covered 2B must be fitted as hung on the cover holding member 10a of the cover holder 10. The operation of fitting the insertion tube tip portion 23B of the aforesaid endoscope to be covered 2B to the inner peripheral surface of the cover tip portion 23A of the aforesaid insertion tube cover portion 11A in this state has proved troublesome.

However, as shown in FIG. 14, if the insertion tube cover portion 11A is fixed on the operation part 12B of the aforesaid endoscope to be covered 2B, in the case of fitting, by only pressing the tip portion 23B of the insertion tube 11B of the endoscope to be covered 2B until it contacts the tip surface on the inner surface of the cover tip portion 23A of the insertion tube cover portion 11A, the fitting will be completed and the fitting maneuverability is high.

Figure 15:
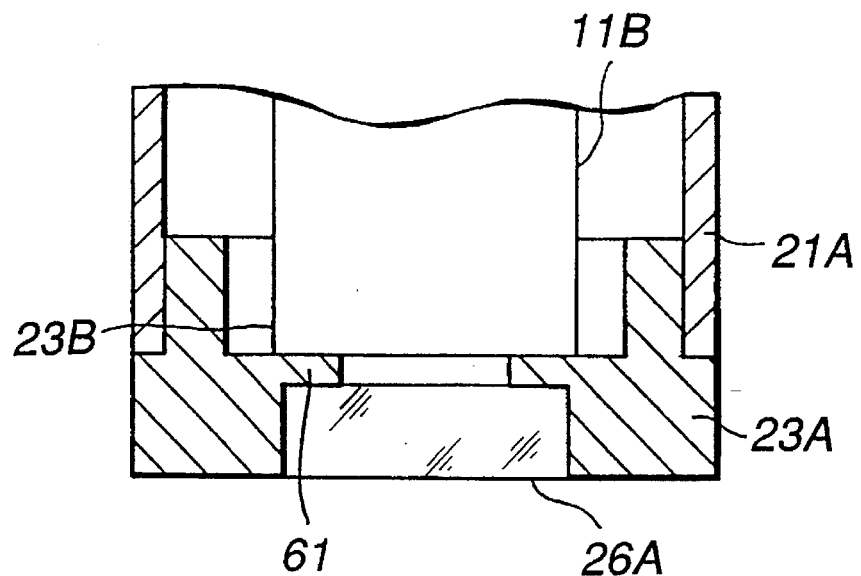
FIG. 15 is a magnified sectional view of an endoscope cover tip portion in the 12th embodiment of the present invention.

FIG. 15 shows the 12th embodiment of the present invention.

As shown in this embodiment, when a contact portion 61 on the tip surface of the insertion tube tip portion 23B of the endoscope to be covered 2B is formed in the cover tip portion 23A holding the transparent plate of the cover observation window 26A, the tip surface of the insertion tube tip portion 23B will no longer contact the transparent plate of the aforesaid cover observation window 26A and therefore the transparent plate can be prevented from being damaged.

FIGS. 16 to 20 show the 13th embodiment of the present invention.

Figure 16:
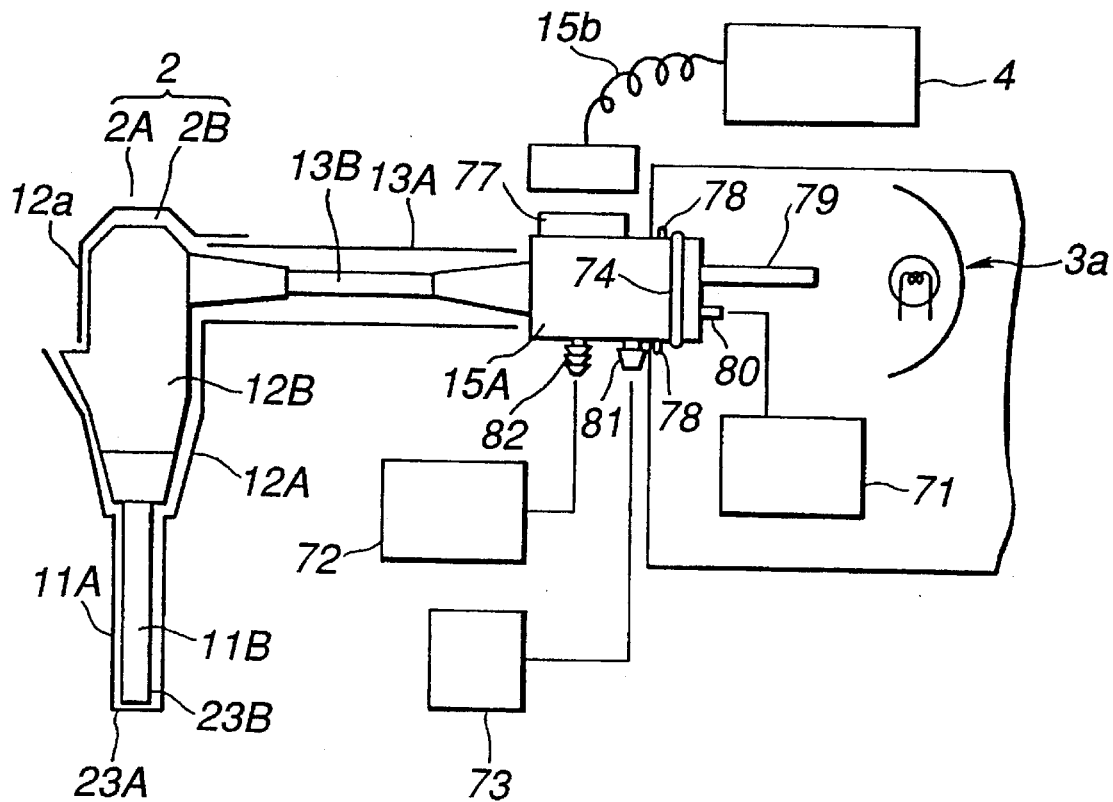
FIGS. 16 to 20 show the 13th embodiment of the present invention.

As shown in FIG. 16, a cover type endoscope apparatus 1 according to this embodiment comprises a channel-less endoscope cover type endoscope (while shall be hereinafter briefly mentioned as the "cover type endoscope") 2 consisting of a channel-less endoscope cover (which shall be hereinafter briefly mentioned as the "endoscope cover") 2A and an endoscope for a channel-less endoscope cover (which shall be hereinafter briefly mentioned as the "endoscope to be covered"), a light source device 3a which feeds an illuminating light to the endoscope 2B to be covered and is an example of an external device for a coverless endoscope, a video processor 4 processing signals for imaging means built-in in the endoscope to be covered 2B and an air supplying device 71, sucking device 72 and water supplying device 73 communicating respectively with an air supplying channel, sucking channel and water supplying channel built-in in the aforesaid endoscope to be covered 2B.

When an endoscope examination is to be made, a clean endoscope to be covered 2B is covered with a clean endoscope cover 2A, after the examination, the endoscope cover 2A is abandoned and, on the other hand, the endoscope to be covered 2B is covered with a new clean endoscope cover 2A and is repeatedly used.

The aforesaid endoscope to be covered 2B comprises a long, narrow, and flexible endoscope insertion tube (which shall be hereinafter briefly mentioned as the "insertion tube") 11B, an endoscope operation part (which shall be hereinafter briefly mentioned as the "operation part") 12B formed on the proximal end portion of the insertion tube 11B and a universal cord 13B extending out of the side of the operation part 12B. An illumination optical system and an observation optical system making the aforesaid imaging means form object images are arranged at the tip of the aforesaid insertion tube 11B. When a connector 15A provided at the distal end of the aforesaid universal cord 13B is connected to a light source device 3 for a coverless endoscope, illuminating light from a lamp within the aforesaid light source device 3 is fed to the aforesaid illumination optical system through a light guide (not illustrated) inserted through the aforesaid universal cord 13B and insertion tube 11B.

The illuminating light fed to the illumination optical system is emitted on the forward object side through a cover illumination window (not illustrated) provided on the end surface of the cover tip portion 23A of the aforesaid insertion tube cover portion 11A provided opposite an illumination window (not illustrated) of the tip portion 23B of the insertion tube 11B.

Such an object as an illuminated affected portion forms an optical image on an imaging surface of such imaging means as a solid state imaging device (SID) arranged in a focal plane through a cover observation window (not illustrated) provided adjacent to the cover illumination window and an observation optical system provided in the insertion tube 11B of the endoscope to be covered 2B arranged opposite and inside the cover observation window.

The optical image formed on this imaging surface is photoelectrically converted, is input into the video processor 4 through a signal cable 15a inserted through the insertion tube 11B and universal cord 13B and is processed to be a signal and then a standard video signal is produced and is input into the monitor 7 to display the object image on a displaying screen.

On the other hand, the endoscope cover 2A is largely divided into an insertion tube cover portion 11A, operation part cover 12A and universal cord cover 13A covering, respectively, the insertion tube 11B, operation part 12B and universal cord 13B of the endoscope to be covered 2B. The insertion tube cover portion 11A, part of the operation part cover 12A and universal cord cover 13A are formed to be integral. The upper portion of operation part cover 12A is opened and this opening portion is closed with a cover lid 12a.

When the aforesaid endoscope to be covered 2B is covered with the aforesaid endoscope cover 2A, first, the insertion tube 11B of the aforesaid endoscope to be covered 2B is inserted into the insertion tube cover portion 11A from the upper opening portion of the endoscope cover 2A and the insertion tube 11B, operation part 12B and universal cord 13B of the endoscope to be covered 2B are covered, respectively. After they are covered as predetermined, the opening portion of the aforesaid endoscope cover 2A is closed with the cover lid 12a.

Such engaging member 74 as a C-ring is provided at the end of the aforesaid connector 15A and is fixed by engaging with an engaging portion 76 provided in a connector insertion port 75 provided in the light source device 3 for the coverless endoscope.

The aforesaid connector 15A is provided with a video connector 77 connected to a video cable 15b transmitting image signals to the aforesaid video processor 4, an electric contact 78 transmitting a light adjusting electric signal for adjusting the illuminating light amount of the light source device 3 transmitted from the aforesaid video processor 4 to the aforesaid light source device 3 through the aforesaid video connector 77 and signal cable 15a and through an electric contact receiving groove 75a provided in the aforesaid connector insertion port 75, a receiving portion 79 receiving the illuminating light emitted from the aforesaid light source device, an air supplying port 80 connecting an air supplying channel supplying air for washing lenses to the tip of the insertion tube 11A of the aforesaid endoscope to be covered 3B and connecting it to the aforesaid air supplying device 71, a water supplying venting cap 81 connected with a water supplying channel for supplying water from the tip of the aforesaid insertion tube 11A and connected to a water supplying device 73 and a sucking venting cap 82 connected to a sucking channel for sucking unwanted contaminants from the tip of the aforesaid insertion tube 11A and connected to a sucking device 72. The channels and wirings connected to the venting caps 81 and 82, electric contact 78, receiving portion 79, air supplying port 80 and video connector 77 are arranged within the aforesaid connector 15A.

The aforesaid light source device 3 and air supplying device 71 may be incorporated in an endoscope controlling apparatus processing electric signals transmitted from the aforesaid endoscope to be covered or transmitting electric signals to the endoscope to be covered 2B and controlling them.

Figure 17:
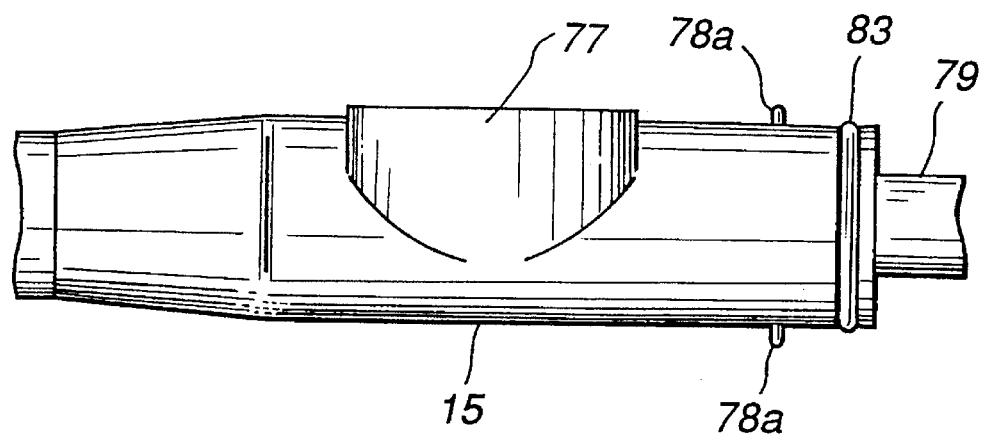

On the other hand, FIG. 17 shows a connector 15 as a connecting portion provided at the distal end of the universal cord 13B which is a connecting portion of an endoscope to be covered with a channeled endoscope cover and connected to an external device (such as a light source device) used for a channeled endoscope cover type endoscope.

In the channeled endoscope cover type endoscope, as forceps channels and sucking channels in contact with the outer surface of the endoscope are provided on the endoscope cover 2A, the aforesaid connector 15 can be made smaller in the diameter by the unnecessary sizes of the air supplying port 8, water supplying venting cap 81 and sucking venting cap 82 than the connector 15A provided in the endoscope to be covered 2B with the aforesaid channelless endoscope cover. Therefore, the connector insertion port of the light source device (not illustrated) for the endoscope to be covered with the channeled endoscope cover connecting the connector 15A can be also made smaller in the diameter than that of the light source device 3a for the aforesaid coverless endoscope.

In the drawing, the connector 15 and the aforesaid universal cord 13B are formed to be of substantially the same outside diameter.

Also, such engaging member 83 as a C-ring is provided at the end of the connector 15 and is fixed by engaging with the engaging portion provided in the connector insertion port provided in the light source device (not illustrated) for the endoscope to be covered with the channeled endoscope cover.

Also, as in the aforesaid connector 15A, the connector 15 is provided with a video connector 77 connecting a video cable 15b, an electric contact 78a transmitting a light adjusting electric signal adjusting the illuminating light amount of the light source device (not illustrated) for the endoscope to be covered with the channeled endoscope cover to the light source device for the endoscope to be covered with the channeled endoscope cover and a receiving portion 79 receiving the illuminating light emitted from the light source device (not illustrated) for the endoscope to be covered with the channeled endoscope cover. The wiring connected to the aforesaid electric contact 78a and receiving portion 79 is provided within the aforesaid connector 15.

The light source device for the endoscope to be covered with the channeled endoscope cover may be incorporated in an endoscope controlling device processing the electric signal transmitted from the aforesaid endoscope to be covered with the channeled endoscope cover or transmitting the electric signal to be controlled to the endoscope to be covered with the channeled endoscope cover.

Since the aforesaid connector 15 and universal cord 13B are formed to be substantially of the same outside diameter, when the endoscope cover 2A is to be applied, the connector 15 does not catch and it is easy to insert or remove the universal cord 13B and connector 15 into or out of the universal cord cover 13A.

On the other hand, reference numeral 84 represents an adapter body which is an example of an endoscope connecting member for connecting the connector 15 provided at the distal end of the universal cord 13B of the endoscope to be covered with the channeled endoscope cover to be used for the channeled endoscope cover type endoscope to the connector insertion port 75 of the light source device 3a for the coverless endoscope. A connector insertion port 84a which is the first connecting portion into which the connector 15 is to be inserted is provided in the axial center of the adapter body 84. The outer periphery of the adapter body 84 forms a light source device connecting portion 84h which is the second connecting portion connected to the connector insertion portion 75 provided in the light source device 3a for the aforesaid coverless endoscope.

An engaging portion 84b engaged with an engaging member 83 provided at the end of the connector 15 is formed on the inner side of the connector insertion port 84a. Further, electric contact receiving grooves 84c connecting to the aforesaid electric contacts 78a are formed within the aforesaid connector insertion port 84a.

Figure 20:
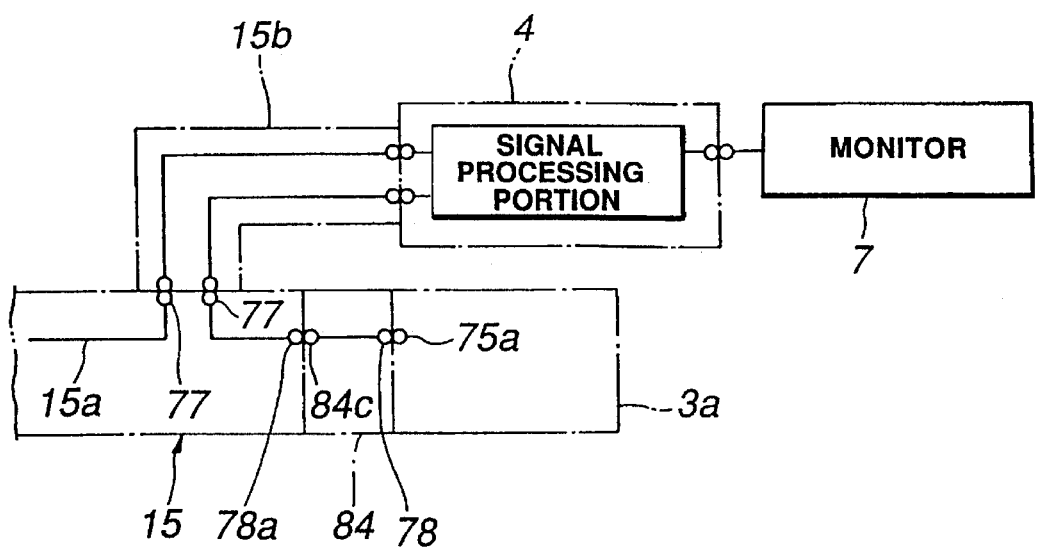

When the aforesaid connector 15 is inserted into the aforesaid connector insertion port 84a, the electric contacts 78a provided on the outer periphery of the connector 15 are inserted into and conduct through the aforesaid electric contact receiving grooves 84c. Also, electric contacts 78 conducting through the electric contact receiving grooves 75a provided in the connector insertion port 75 of the light source device for the aforesaid coverless endoscope and conducting through the electric contact receiving grooves 84c on the aforesaid adapter body 84 are provided on the outer periphery of the adapter body 84. Their wiring is shown in FIG. 20.

Further, the engaging member 83 of the aforesaid connector 15 is engaged with the engaging portion 84b and the aforesaid adapter body 84 is fixed to the aforesaid connector 15. Such engaging member 83 as a C-ring engaging with the aforesaid engaging portion 76 is provided on the outer periphery of the aforesaid adapter body 84. Further, a positioning rod 84 for positioning in the case of inserting and fixing the adapter body 84 in the connector insertion port 75 of the light source device 3a for the aforesaid coverless endoscope is provided to project on the end surface of the adapter body 84. The positioning rod 84d is provided in the same position and size as of the air supplying port 80 provided in the aforesaid connector 15A.

The operation of the aforesaid embodiment will be explained below:

When the connector 15 provided at the distal end of the universal cord 13B of the endoscope to be covered with the channeled endoscope cover used for the channeled endoscope cover type endoscope is to be connected to the light source device 3a for the coverless endoscope, the adapter body 84 is first fitted and fixed to the connector 15 and then the electric contacts 78a of the connector 15 are caused to conduct through the electric contact receiving grooves 84c of the aforesaid adapter body 84.

Then, the light source device connecting portion 84h provided on the outer periphery of the aforesaid adapter body 84 fitted to the aforesaid connector 15 is inserted into the connector insertion port 75 provided in the light source device 3a for the aforesaid coverless endoscope. Then, the receiving portion 79 projecting out of the aforesaid connector 15 is inserted through the light source device 3a for the aforesaid coverless endoscope and the positioning rod 84d is positioned and fixed.

The electric contacts 78 conducted through the aforesaid electric contact receiving grooves 84c are caused to conduct through the electric contact receiving grooves 75a provided in the connector insertion port 75 of the light source device 3a for the aforesaid coverless endoscope.

As a result, the connector 15 provided at the distal end of the universal cord 13 of the endoscope to be covered with the channeled endoscope cover used for the channeled endoscope cover type endoscope can be connected to the light source device 3a for the coverless endoscope. When the endoscope to be covered with the channeled endoscope cover is to be used, the conventional light source device can be used, the exclusive device is not required and the interchangeability is high.

Figure 21:
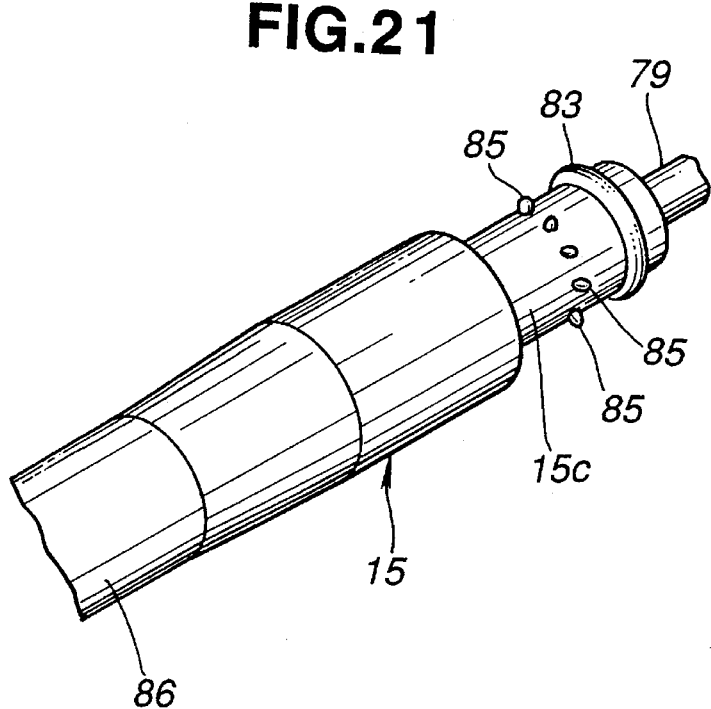
FIG. 21 is a perspective view of a cover type endoscope side connector in the 14th embodiment of the present invention.

FIG. 21 shows the 14th embodiment of the present invention.

As shown in this embodiment, if a level difference portion 15c is provided on a connector 15 and video contacts 85 having a length housed within the outer diameter of the connector 15 are provided on the outer periphery of the level-difference portion 15c, the video connector 77 of the connector 15 shown in FIG. 17 can be formed using only pins. For the portion of the video connector 77, the connector 15 can be made smaller and the diameter of an universal cord 86 joined to the connector 15 can be made narrower.

If the connector 15 can be made smaller and the diameter of the universal cord 86 can be made narrower, an insertion operation of an engaging member 83 provided on the level-difference portion 15c can be easier and a video processor 4 can be made smaller.

Figure 22:
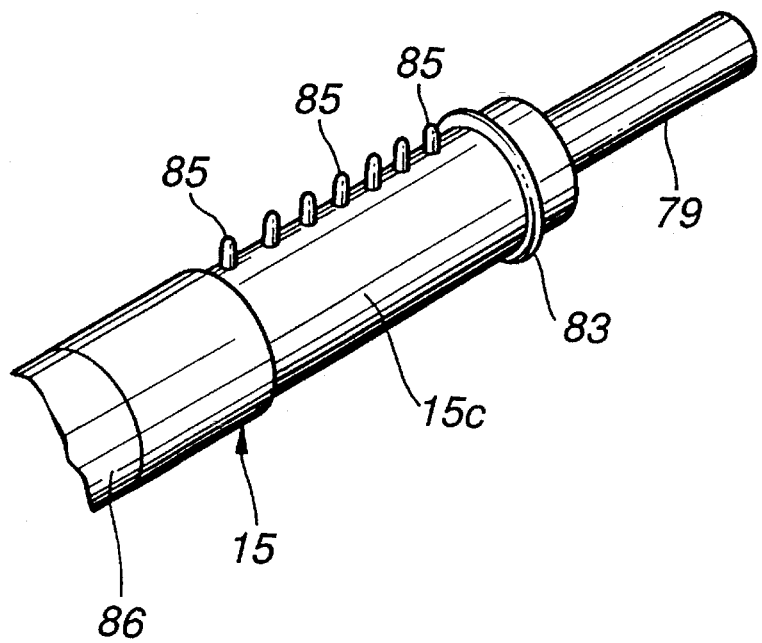
FIG. 22 is a perspective view of a cover type endoscope side connector in the 15th embodiment of the present invention.

FIG. 22 shows the 15th embodiment of the present invention.

As shown in this embodiment, if the aforesaid video contacts 85 are arranged in a single line along the axis direction on the connector 15 and a level-difference portion 15c is provided in only one portion where the video contacts 85 are provided, the projected amount of the video contacts 85 may be about half of the number of the video contacts 85 arranged around the level-difference portion 15c as shown in FIG. 21. Thus, the connector 15 can be made much smaller and the diameter of the universal cord 86 can be made narrower.

Figure 23:
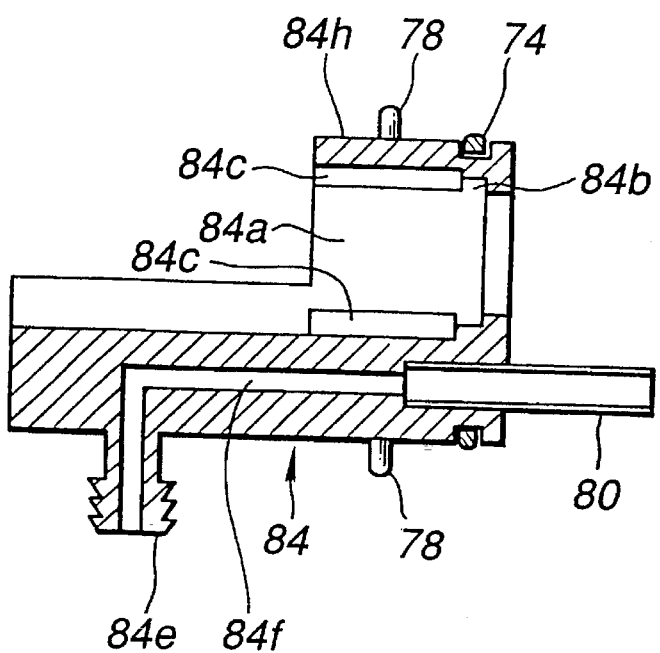
FIG. 23 is a sectional view of an adapter body in the 16th embodiment of the present invention.

FIG. 23 shows the 16th embodiment of the present invention.

Figure 18:
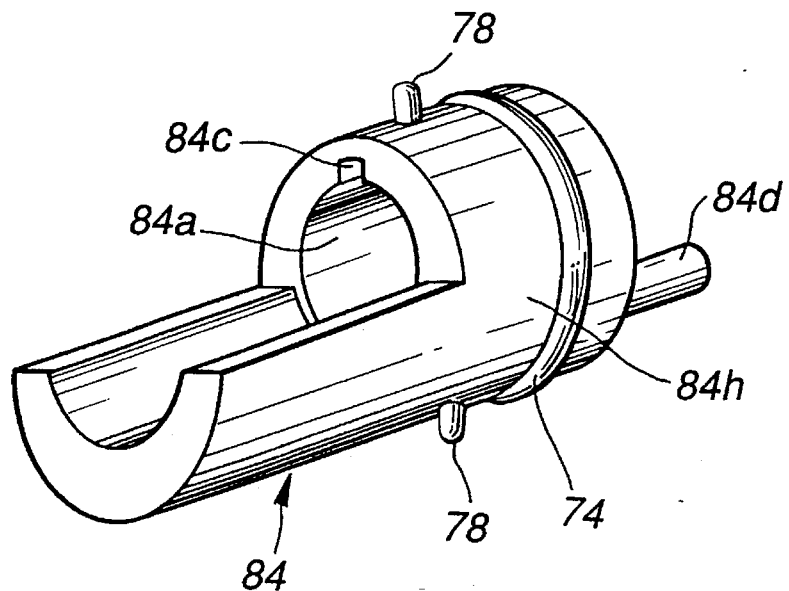
Figure 19:
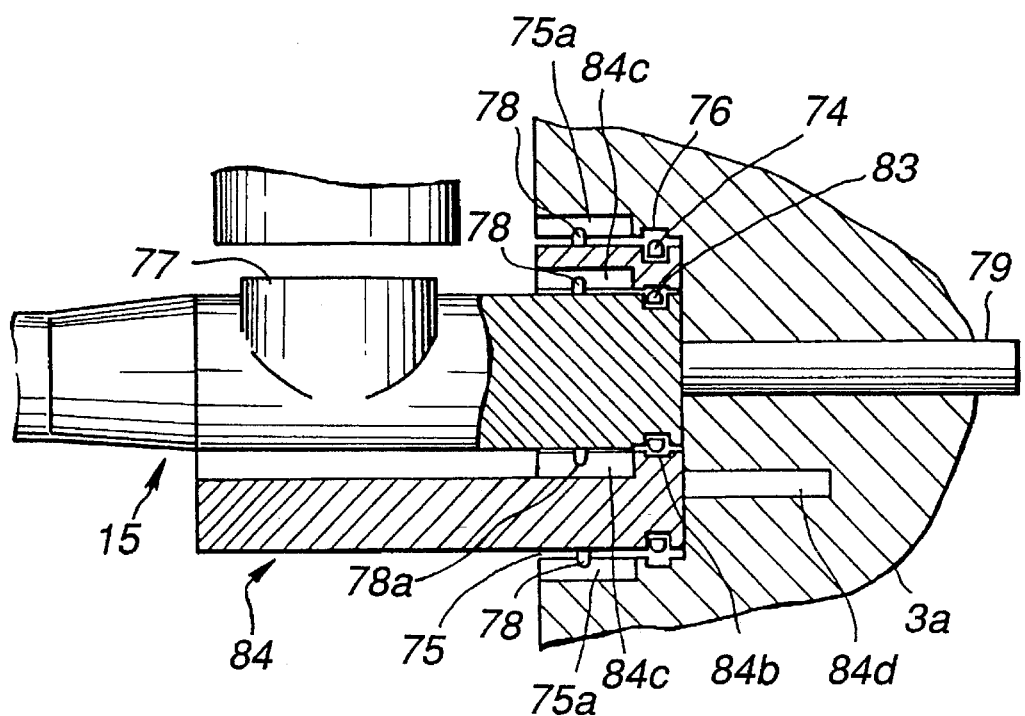

In the embodiment shown in FIG. 18, a positioning rod 84d is projected from the end surface of an adapter body 84. As shown in FIG. 23, instead of the positioning rod 84d, a supplying air port 80 is provided and a supplying air venting cap 84e is provided in the adapter body 84, so that the supplying air venting cap 84e and the supplying air port 80 are joined through a supplying air channel 84f. Further, a supplying air channel provided in an endoscope cover with channels (not illustrated) is connected to the aforesaid supplying air venting cap 84e.

The air supplied from a supplying air device 71 (see FIG. 16) is supplied to a supplying air channel provided in an endoscope cover with channels (not illustrated) through the supplying air port 80, the supplying air channel 84f and supplying air venting cap 84e.

In this embodiment, because the supplying air device 71 can be used as it is, an exclusive device is not needed.

Figure 24:
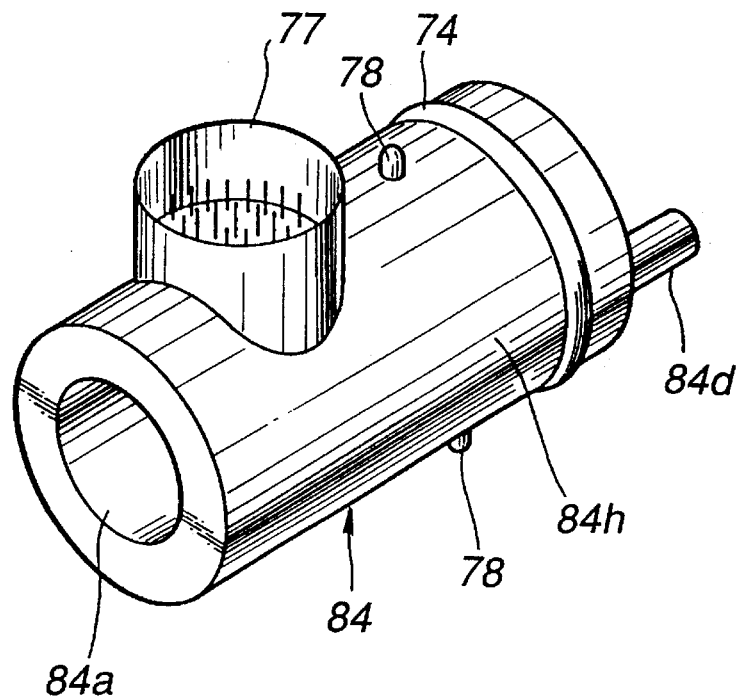
FIGS. 24 to 26 show the 17th embodiment of the present invention.
Figure 25:
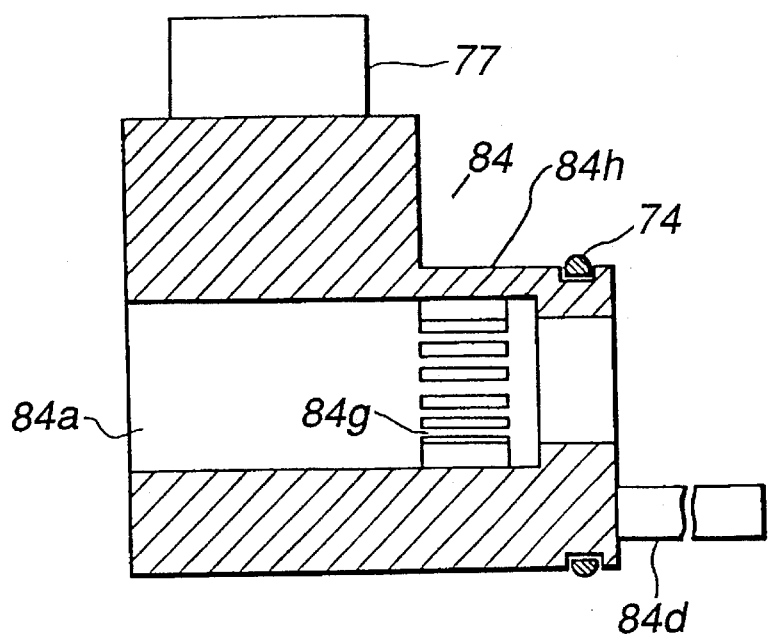
Figure 26:
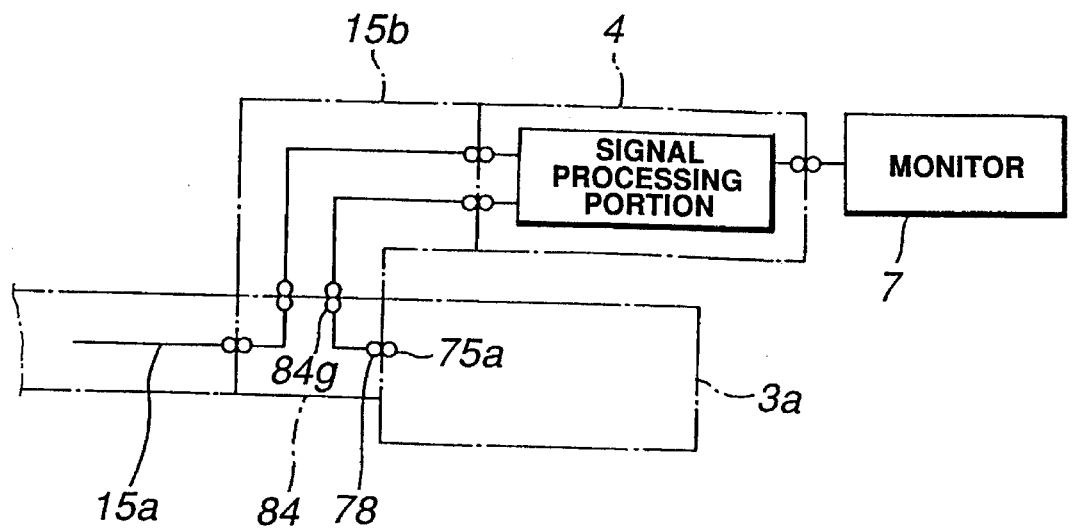

FIGS. 24–26 show the 17th embodiment of the present invention.

In an adapter body 84 shown in t,his embodiment, a video connector 77 connected to a video cable 15b which transmits image electric signals to a video processor 4 is provided and a video contact receiving groove 84g is provided which is electrically connected to the video connector 77 to receive an inner periphery of the connector insertion port 84a. The connector 15 shown in FIG. 21 can be fitted and fixed to thee adapter body 84. The video connector 77 and an electric contact 78 are electrically connected, so that the electric signal received by the video connector 77 is transmitted to the electric contact 78.

When the adapter body 84 is fitted to the connector 15 shown in FIG. 21, the video contacts 85 are fitted into the video contact receiving groove 84a of the adapter body 84, so that the video contacts 85 and video contact receiving groove 84a are electrically connected.

The image electric signals transmitted in an endoscope to be covered (not illustrated) make the video contacts 85 and video contact receiving groove 84a conductive and are transmitted to the video processor 4 through the video connector 77 and a video cable 15b. At the same time, light adjusting electric signals generated from a video processor 4 and transmitted through the video connector 77 and video cable 15b are transmitted to a coverless endoscope light source device 3a through the electric contact 78 (see FIG. 26).

As a result, by using the adapter body 84, the connector 15 from which the video connector 77 is removed for miniaturizing the connector can be connected to the coverless endoscope light source device 3a.

The video contact receiving groove 84g provided in the connector insertion port 84a of the adapter body 84 may be provided in a single line so as to be able to fit the connector 15 shown in FIG. 22.

Figure 27:
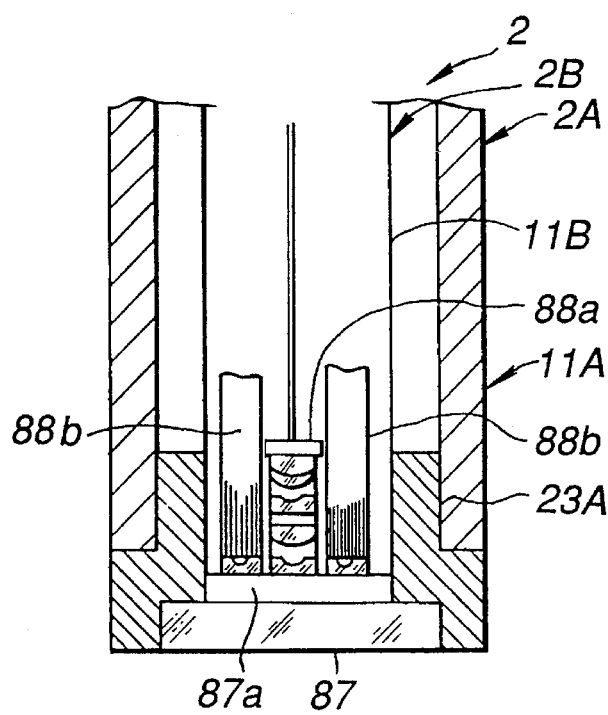
FIGS. 27 and 28 show the 18th embodiment of the present invention.
Figure 28:
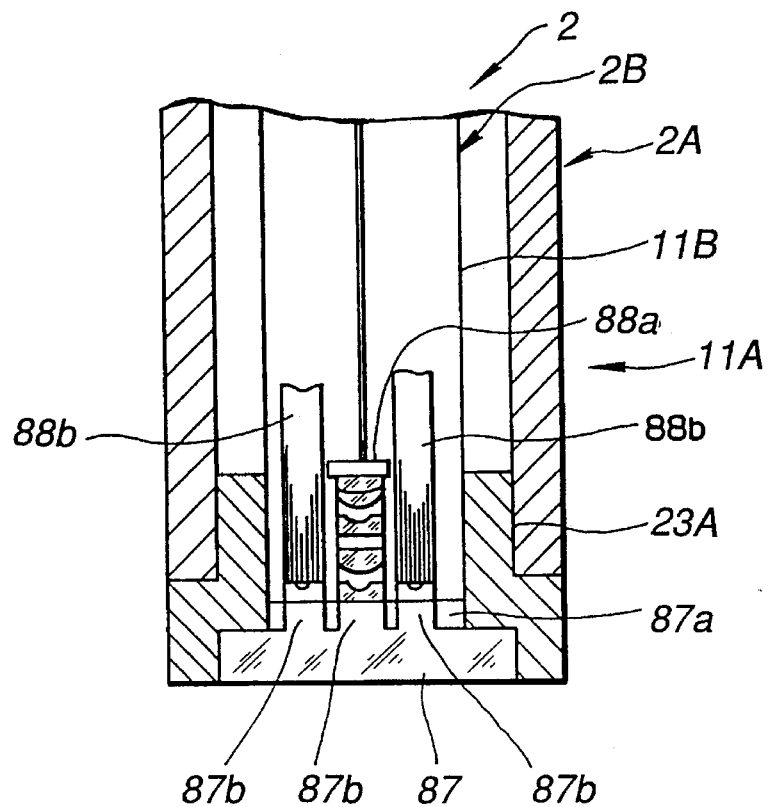

FIGS. 27 and 28 show the 18th embodiment of the present invention.

As shown in FIG. 27, in a general cover type endoscope 2, a tip portion 23B of the insertion tube 11B of an endoscope to be covered 2B is held by a cover tip portion 23A of the insertion tube cover portion 11A of the endoscope cover 2A. Then, an opening 87a is formed between the tip portion 23B and a cover glass 87 provided at the cover tip portion 23A. When the endoscope to be covered 2B is inserted into the endoscope cover 2A, a deterioration of the observation ability is prevented so that dust which enters during insertion of the aforesaid endoscope to be covered 2B is not caught between an imaging optical system 88a provided at the tip portion 23B and the cover glass 87.

However, illuminating light which radiates from an illumination optical system 88b provided at the tip portion 23b of the endoscope to be covered 2B is reflected by the cover glass 87 and enters the imaging optical system 88a, because the opening 87a is provided. Thus, the observation capability is lowered due to flare.

Therefor, as shown in FIG. 28, a convex portion 87b is formed on a surface of the cover glass 87 opposing the imaging optical system 88a of the cover glass 87 and the illumination optical system 88b, and the imaging optical system 88a and illumination optical system 88b are fitted to the convex portion 87b of the cover glass 87, so that a deterioration of the observation capability can be prevented. In addition, since the dust entering at fitting the endoscope to be covered 2B falls in the opening 87a formed around the convex portion 87b, the dust is not caught among the convex portion 87b of the cover glass 87, the imaging optical system 88a and the illumination optical system 88b.

Figure 29:
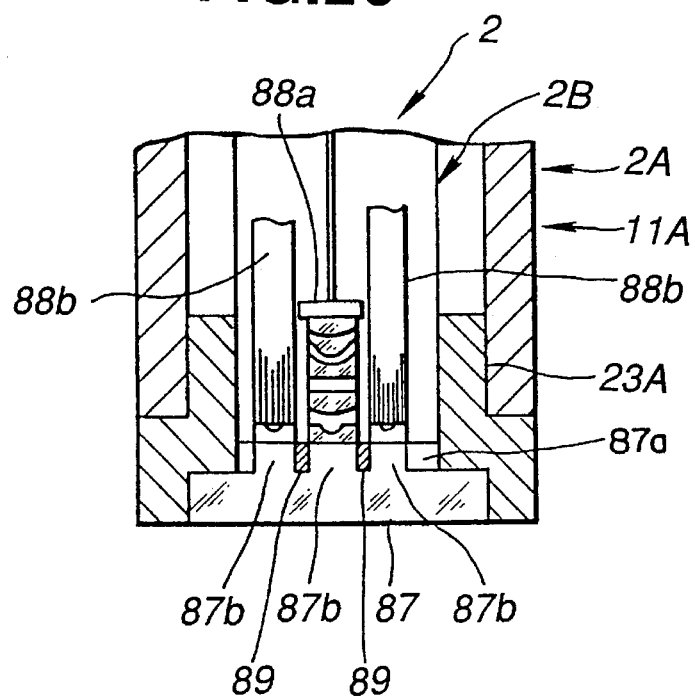
FIG. 29 is a sectional view of a cover type endoscope tip portion in the 19th embodiment of the present invention.

FIG. 29 shows the 19th embodiment of the present invention.

As shown in this embodiment, a colored portion 89 by, for example, black ink, is filled up in the opening 87a between the convex portions 87b of the cover glass 87, so that flare can be prevented.

Figure 30:
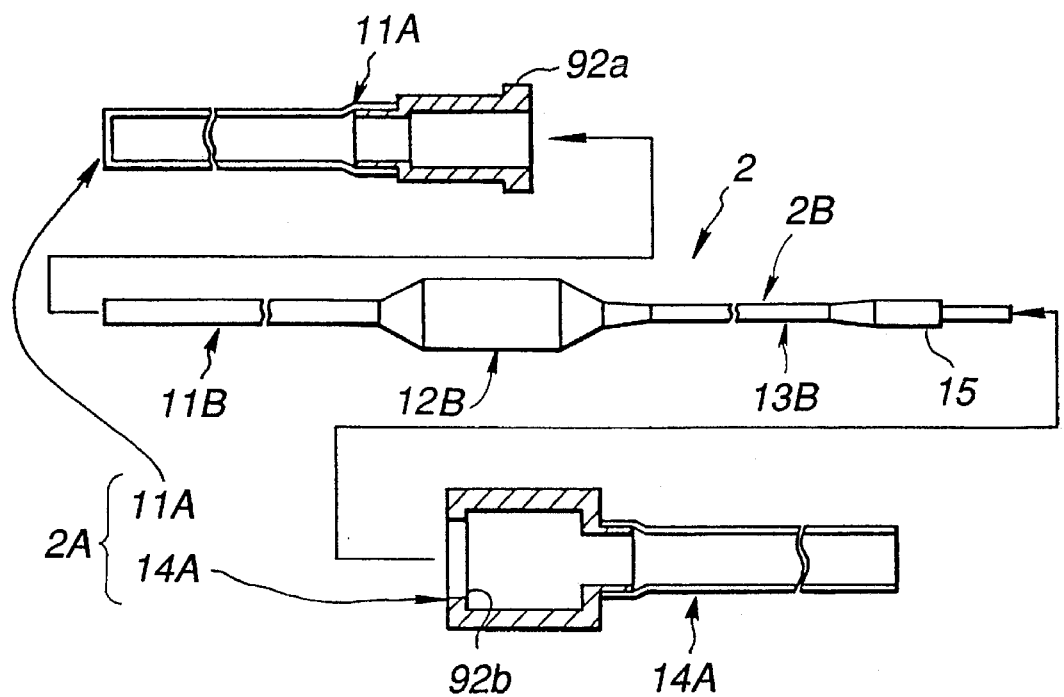
FIGS. 30 and 31 show the 20th embodiment of the present invention.
Figure 31:
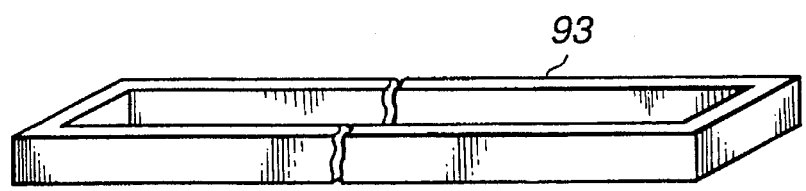

FIGS. 30 and 31 show the 20th embodiment of the present invention.

Reference numeral 2 in FIG. 30 represents an endoscope cover type endoscope (hereinafter, "cover type endoscope"). The cover type endoscope comprises an endoscope cover 2A and an endoscope to be covered 2B fitted to the endoscope cover 2A.

The endoscope to be covered 2B comprises a long, narrow, flexible endoscope insertion tube (hereinafter, "insertion tube") 11B, and endoscope operation part (hereinafter, "operation part") 12B formed in the proximal portion of the insertion tube 11B, an universal cord 13B which is an example of the connecting cord extended from the operation part 12B and a connector 15 provided at the end of the universal cord 13B.

The insertion tube 11B, operation part 12B, universal cord 13B and connector 15 which form the endoscope to be covered 2B are arranged in an approximately straight line.

The operation part 12B is a portion to be held when the endoscope is used. The operation part 12B is provided with a drive controlling portion of a fluid controlling device (not illustrated) which is one of the external controlling devices for controlling sucking and supplying air and water, and a bending operation part (not illustrated) for controlling and operating a bent portion provided at the tip of the insertion tube 11B.

The universal cord 13B is a connecting member between the operation part 12B and the connector 15. The connector 15 connects the external devices, such as a light source device and video processor and the endoscope to be covered 2B. The illuminating light originating from the light source device is transmitted to the tip portion 23B of the insertion tube 11B of the endoscope to be covered 2B through the connector 15. An image obtained by the solid state imaging device arranged at the rear of the observation window of the tip portion 23B is converted into electric signals. Then, the signals are transmitted to the video processor through the connector 15.

At the same time, the endoscope cover 2A comprises an insertion tube cover portion 11A and an operation part universal cord cover 14A. The insertion tube 11A, operation part 12B and universal cord 13B of the endoscope to be covered 2B are arranged in a straight line and covered with the endoscope cover 2A.

The insertion tube cover portion 11A comprises an insertion tube cover outer cover 21A covering the insertion tube 11B, a connector for fixing the endoscope operation part 22A airtightly provided at the proximal end of the insertion tube cover outer cover 21A and a cover tip portion 23A airtightly provided at the distal end of the insertion tube cover outer cover 21A.

Further, engaging portions 92a and 92b which can be engaged with each other are provided on an opposing surface between the insertion tube cover portion 11A and operation part universal cord cover 14A. Then, the endoscope cover 2A which is disinfected is packaged.

Reference numeral 93 represents a clean endoscope cover tray which is used when the endoscope cower 2A is fitted to the endoscope to be covered 2B. The endoscope cover tray 93 is a rectangular shape which is suited for housing the endoscope to be covered 2B.

Next, the effect of the embodiment will be explained.

A fitting operation of the endoscope cover 2A to the endoscope to be covered 2B is performed in the clean endoscope cover tray 93.

First, the end of the insertion tube 11B of the endoscope to be covered 2B is inserted into the insertion tube cover portion 11A of the endoscope cover 2A. A connector 15 is inserted into the operation part universal cord cover 14A of the endoscope cover 2A.

Next, an engaging portion 92a formed at the opening end of the insertion tube cover portion 11A and an engaging portion 92b formed at the opening end of the operation part universal cord cover 14A are engaged. Then, the whole endoscope to be covered 2B is covered with the insertion tube cover portion 11A and operation part universal cord cover 14A.

In this way, the endoscope to be covered 2B is formed in an approximately straight line. Thus, the endoscope cover 2A may be composed of only two kinds of insertion tube cover portions 11A and operation part universal cord cover 14A. Accordingly, the number of parts is reduced and, further, the fitting operation of the endoscope cover 2A to the endoscope to be covered 2B becomes simple.

In addition, because of the rectangular shape of the endoscope cover tray 93, the tray does not take up a lot of space when it is housed and fitted. Therefore, the tray can be easily handled.

Figure 32:
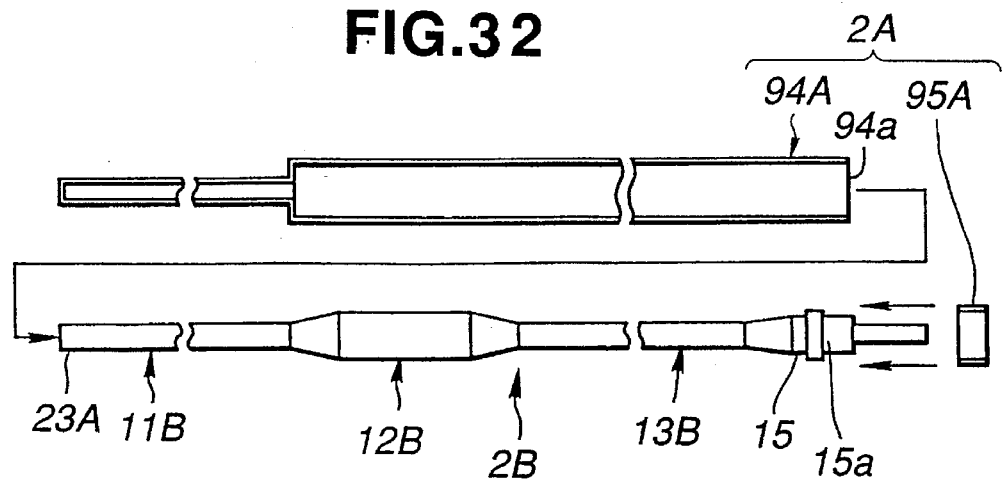
FIGS. 32 and 33 show the 21st embodiment of the present invention.
Figure 33:
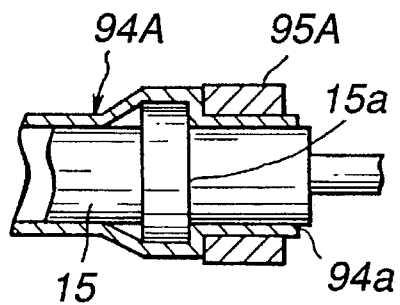
Figure 34:
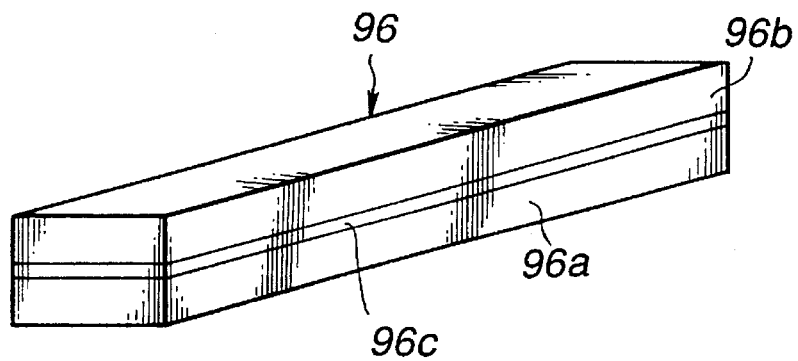
Figure 35:
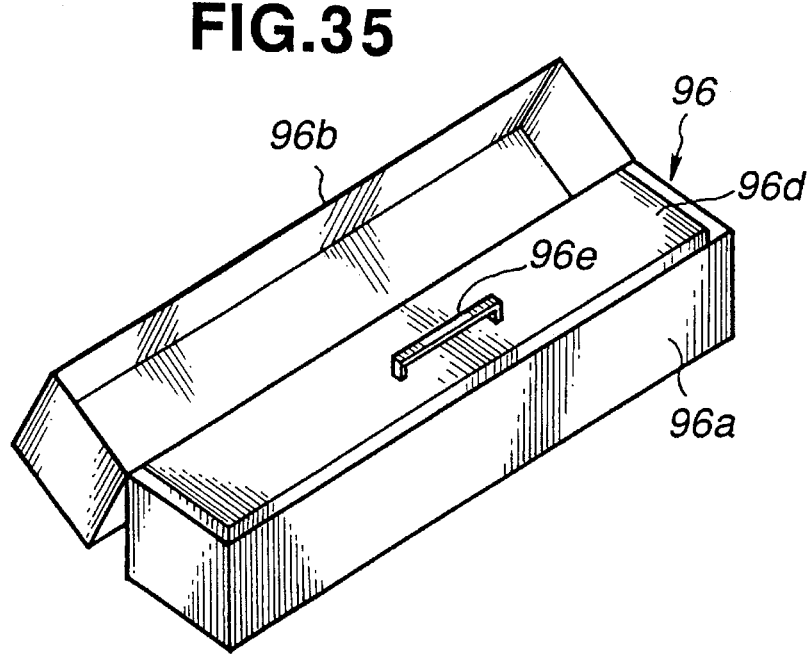

FIGS. 32 and 33 show the 21st embodiment of the present invention.

In this embodiment, a ring-shaped level-difference portion 15a is provided on a connector 15 of an endoscope to be covered 2B. An endoscope cover 2A to be fitted to the endoscope to be covered 2B is composed of an integrated type endoscope cover 94A for covering the whole endoscope to be covered and an engaging tool 95A for fixing the integrated type endoscope cover 94A to the endoscope to be covered 2B. The engaging tool 95A is a ring-shaped elastic material preferably made of metal, resin, or rubber.

When the endoscope to be covered 2B is fitted to the integrated endoscope cover 94A, first, a tip portion 23A of an insertion tube 11B of the endoscope to be covered 2B is inserted into an opening end 94a of the integrated type endoscope cover 94A and then, a tip portion 94a of an insertion tube 11A is inserted into the tip direction of the integrated type endoscope cover 94A. Then, the opening end 94a of the integrated type endoscope cover 94A is led to the connector 15, so that the opening portion 94a is fixed to the level-difference portion 15a formed on the connector 15 by the engaging tool 95A. The fitting operation is performed on the endoscope cover tray 93 shown in FIG. 31.

By this embodiment, the fitting operation is completed only by inserting the endoscope to be covered 2B into the integrated type endoscope cover 94A from one end. Thus, maneuverability is good. Further, the number of parts of the endoscope cover 2A can be much reduced.

FIGS. 34–36(a), (b) and (c) show the 22nd embodiment of the present invention.

In this embodiment, a cover package 96 which houses the endoscope cover 2A is used as an endoscope cover tray.

The center of the cover package 96 is opened out like a book. The cover package 96 is divided into a first housing case 96a and second housing case 96b. The junction of both housing cases 96a and 96b is sealed by a peel-away 96c.

When the peel-away 96c is opened, the cover package 96 is opened out like a book to be divided into the first housing case 96a and second housing case 96b. The inside of the first housing case 96a is disinfected to be clean. In the first housing case 96a, a disinfected and clean endoscope cover 2A is housed and held. The first housing case 96a is sealed by a housing cover 96d(FIG. 36(a)).

When the endoscope cover 2A housed in the first housing case 96a covers an endoscope to be covered, first of all, an used endoscope cover 91A, which is contaminated and removed from the aforesaid endoscope to be covered, is housed in the second housing case 96b.

Next, a housing cover 96d is opened by holding a holding portion 96e provided on the housing cover 96d. Then, the housing cover 96d covers the second housing case 96d. As a result, a clean endoscope cover 2A is exposed out of the first housing case 96a. At the same time, an used endoscope cover 91A is hidden by the housing cover 96d(FIG. 36(b)).

Because the housing cover 96d is opened by holding the holding portion 96e, the outer periphery of the cover package 96, the inner periphery of the first housing case 96a and endoscope cover 2A are not directly touched. Thus, the inner periphery of the first housing case 96a and the endoscope cover 2A are not contaminated.

Then, the first housing cover 96a is used as an endoscope cover tray where the endoscope cover 2A covers an endoscope to be covered.

After that, the first housing case 96a covers the second housing case 96b, and then, the cover package 96 itself is thrown away.

In this way, the utilization of the cover package 96 as an endoscope cover tray saves time to transfer the endoscope cover 2A to another endoscope cover tray in order to cover an endoscope to be covered and improves maneuverability. Further, an used endoscope cover 91A can be easily thrown away.

Figure 37A:
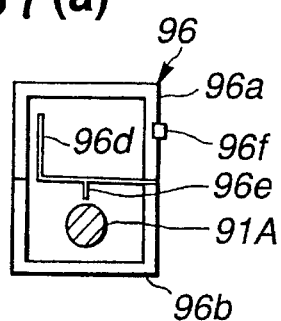
FIGS. 37(a) and 37(b) are sectional views of a cover package in respective states in the 23rd embodiment of the present invention.

FIG. 37 shows the 23rd embodiment of the present invention.

As shown in this embodiment, the aforesaid cover package 96 may be formed of a hollow sheet. Air ill the first housing case 96a and second housing case 96b can be easily discharged by removing an air valve 96f which is an example of attached discharging means.

Figure 37B:
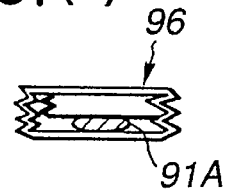

Then, as shown in FIG. 37(b), the cover package 96 from which air is discharged can be compressed by applying force. Therefore, the package is not bulky when it is thrown away.

Figure 38A:
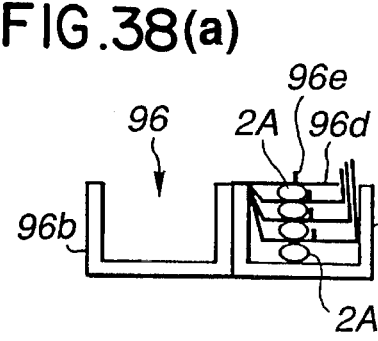
FIGS. 38(a) and 38(b) are sectional views of a cover package in respective states in the 24th embodiment of the present invention.
Figure 38B:
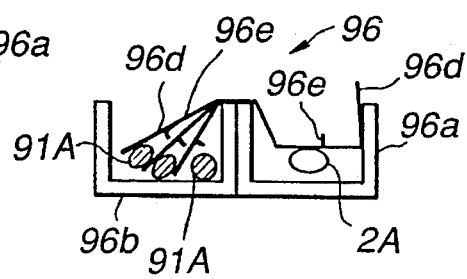

FIGS. 38(a) and 38(b) show the 24th embodiment of the present invention.

As shown in this embodiment, a plurality of housing covers 96d are arranged in the first housing cover 96a. A plurality of endoscope covers 2A may be housed in a laminated state through the housing covers 96d. Because a plurality of the endoscope covers 2A are contained in one cover package 96, the number of cover packages 96 can be reduced and packaging expenses can be cut down. Further, used endoscope covers 91A can be alternately housed in the second housing case 96b with the housing covers 96d, so that efficiency is high.

Figure 39:
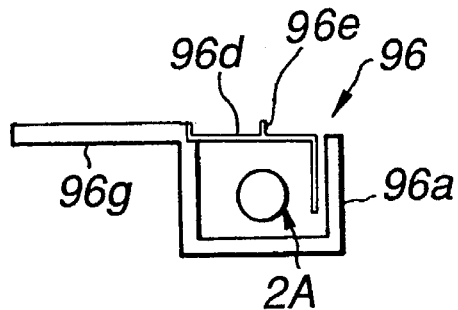
FIG. 39 is a sectional view of a cover package in the 25th embodiment of the present invention.

FIG. 39 shows the 25th embodiment of the present invention.

Figure 36A:
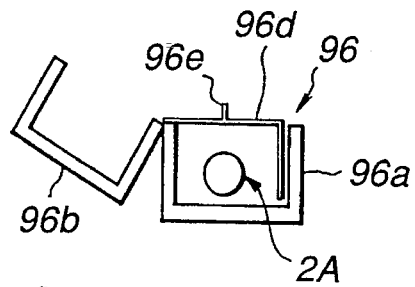
FIGS. 36(a), 36(b) and 36(c) are sectional views of a cover package in respective states.
Figure 36B:
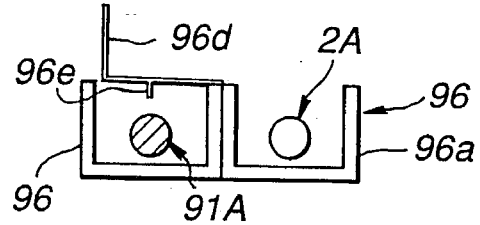
Figure 36C:
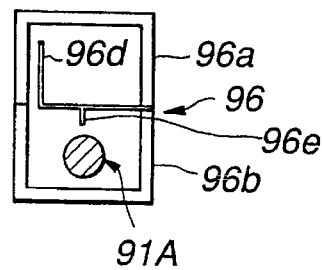

As shown in this embodiment, the second housing case 96b shown in FIG. 36 is formed to be a flat case lid 96g, so that a package can be smaller.

Further, endoscope covers 2A housed in the cover packages 96 shown in FIGS. 34–39 may be either an universal cord type extended from a side of an operation part or a straight line shown in FIGS. 30 and 32.

Figure 40:
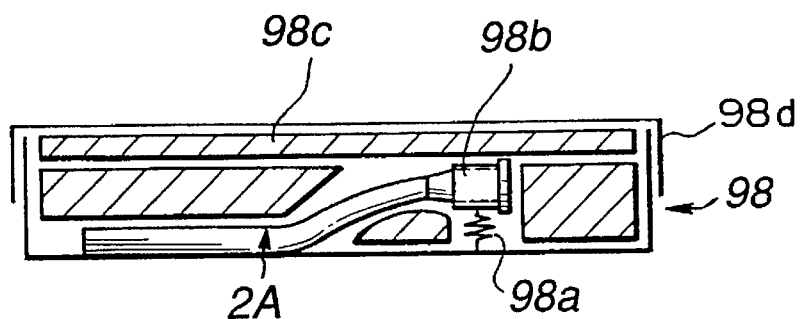
FIGS. 40 and 41 show the 26th embodiment of the present invention.
Figure 41:
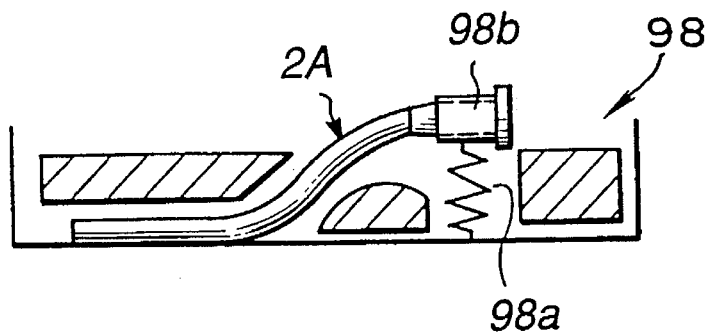

FIGS. 40 and 41 show the 26th embodiment of the present invention.

This embodiment explains an example of a packaging case 98.

The packaging case 98 serves as an endoscope cover tray in the same way of the cover package 96.

The end of a disinfected and clean endoscope cover 2A is held by a cover holder 98b attached to an applying force member 98a, such as a spring, compressed by a packaging lid 98d through a packaging spacer 98c and packaged (the state in FIG. 40).

When the packaging lid 98d is opened to use the endoscope cover 2A, the cover holder 98b is projected by elastic force of the applying force member 98a. Then, the end portion of the endoscope cover 2A held by the cover holder 98b springs out of the packaging case 98.

As a result, the endoscope cover 2A can cover an endoscope to be covered without touching the endoscope 2A. Since the packaging case 98 serves as an endoscope cover tray as it is, the packaging case 98 can be easily handled.

Figure 42:
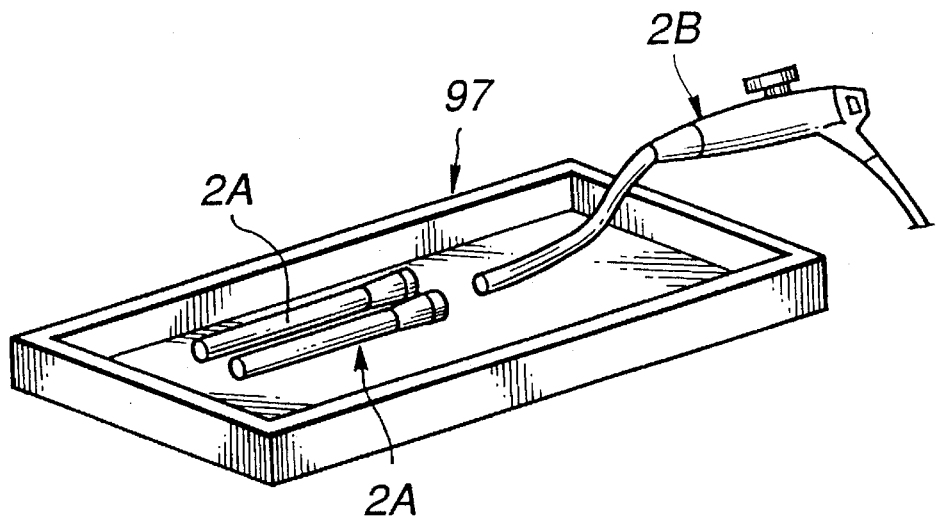
FIG. 42 is a perspective view of an endoscope cover tray in the 27th embodiment of the present invention.

FIG. 42 shows the 27th embodiment of the present invention.

An endoscope cover tray 97 shown in this embodiment can house an endoscope cover 2A and is a rectangular shape having enough capacity for covering an endoscope to be covered 2B. On the endoscope cover tray 97, a plurality of endoscope covers 2A to be used are prepared and the endoscope to be covered 2B from which an used endoscope cover is removed is placed and then, the endoscope cover 2A is fitted to the endoscope to be covered 2B by using clean hands.

As related art, there is the art in which an endoscope cover 2A covers an endoscope to be covered 2B when the endoscope cover 2A is hung on a cover holder. However, attention has to be paid during the covering operation so as not to soil the endoscope cover 2A by touching a floor, so that maneuverability is low. In this invention, because the covering operation is carried out on an endoscope cover tray 97, endoscope covers 2A to be used can be previously prepared and the endoscope cover tray 97 becomes an indicator indicating an clean range. Further, the covering operation can be easily performed in a clean state.

Figure 43:
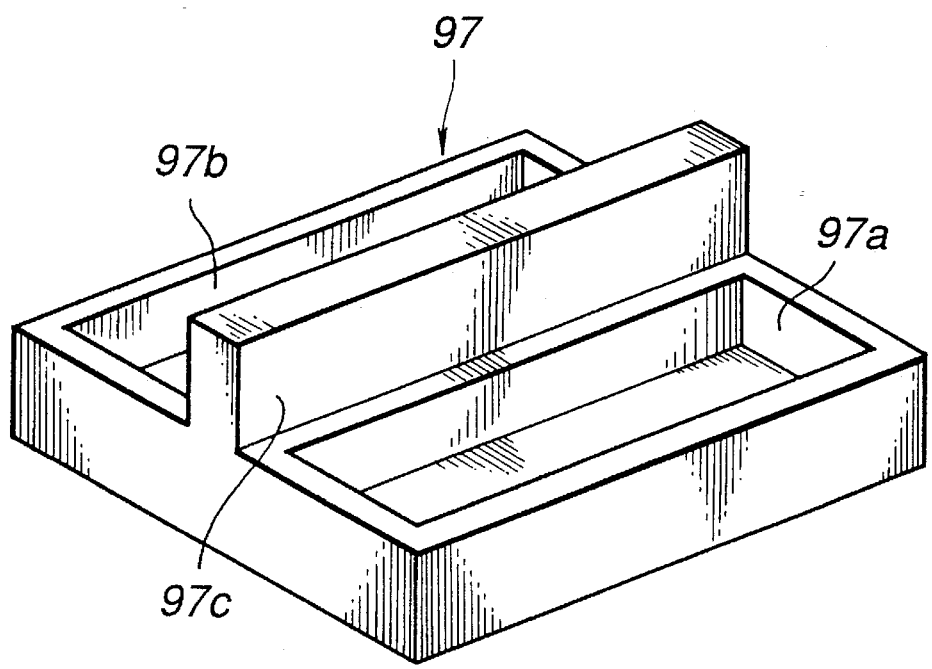
FIG. 43 is a perspective view of an endoscope cover tray in the 28th embodiment of the present invention.

FIG. 43 shows the 28th embodiment of the present invention.

As shown in this embodiment, the aforesaid endoscope cover tray 97 is provided with a fitting operation tray portion 97a and removing operation tray portion 97b. Both tray portions 97a and 97b are divided by an insulating wall 97c which is an insulating portion, so that a clean range (fitting operation tray portion 97a) and an unclean range (removing operation tray portion 97b) can be divided on an endoscope cover tray 97.

A used endoscope cover is removed from an endoscope to be covered in the removing operation tray portion 97b and left on the removing operation tray portion 97b.

On the other hand, on the fitting operation tray portion 97a, the endoscope to be covered from which an used endoscope cover is removed is covered with a clean endoscope cover prepared on the fitting operation tray portion 97a.

As a result, an endoscope cover can be fitted to and removed from an endoscope to be covered on an endoscope cover tray 97.

Figure 44:
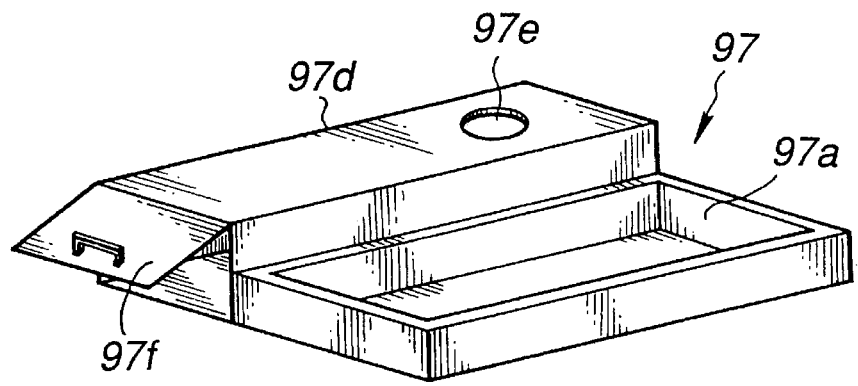
FIGS. 44 and 45 show the 29th embodiment of the present invention.
Figure 45:
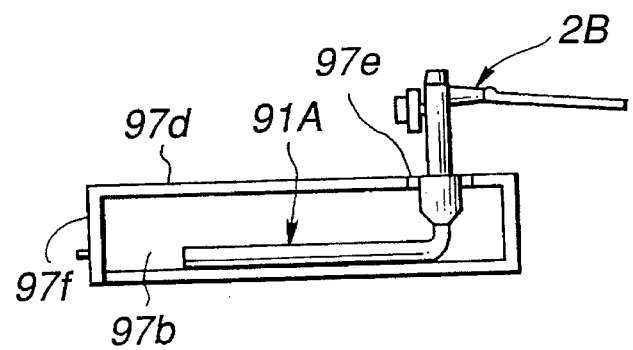

FIGS. 44 and 45 show the 29th embodiment of the present invention.

As shown in this embodiment, the whole periphery of a removing operation tray portion 97b of the endoscope cover tray 97 may be covered with a cover 97d.

For removing an used endoscope cover 91A, first, the used endoscope cover 91A to which an endoscope to be covered 2B is attached is removed from an opening portion 97e opening into the cover 97d and inserted into the removing operation tray portion 97b.

Next, the used endoscope cover 91A is pressed at the port of the opening portion 97e and the endoscope to be covered 2B is removed from the used endoscope cover 91A. Then, the removed endoscope cover 91A is left on the removing operation tray portion 97b. Further, any structure can be used for the opening portion only if the structure can hold and open the elastic endoscope cover 91A.

Then, the endoscope to be covered 2B from which the used endoscope cover 91A is removed is fitted to a clean endoscope cover, which has been previously prepared, on a fitting operation tray portion 97a provided by the side of the removing operation tray portion 97b, and used.

At the same time, the used endoscope cover 91A left on the removing operation tray portion 97b can be suitably eliminated by opening a lid 97f and thrown away.

An unclean range can be surely isolated from a clean range (fitting operation tray portion 97a) by covering the whole periphery of the removing operation tray portion 97b with a cover 97d.

Figure 46:
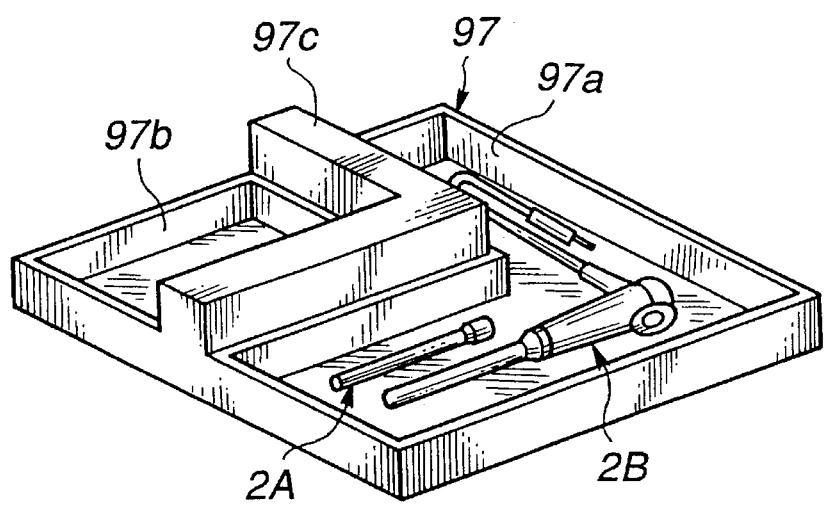
FIG. 46 is a perspective view of an endoscope cover tray in the 30th embodiment of the present invention.

FIG. 46 shows the 30th embodiment of the present invention.

As shown in this embodiment, an L shape of a fitting operation tray 97a can house an universal cord 13B extended from the side of an operation part 12B provided in an endoscope to be covered 2B, so that maneuverability for covering is improved.

Figure 47:
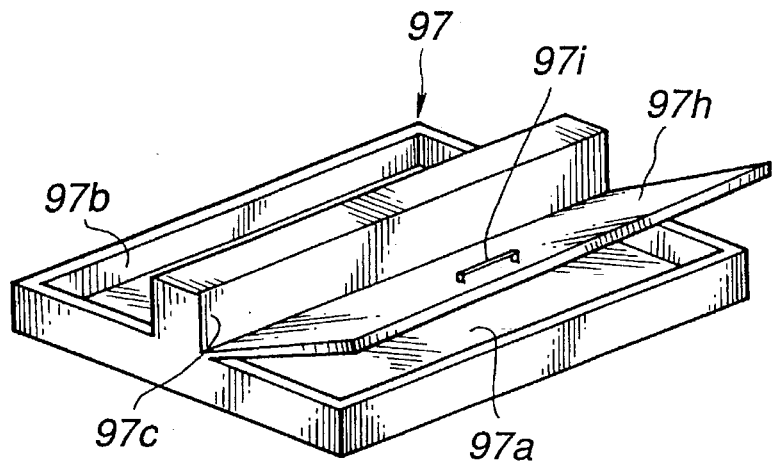
FIG. 47 is a perspective view of an endoscope cover tray in the 31st embodiment of the present invention.

FIG. 47 shows the 31st embodiment of the present invention.

As shown in this embodiment a fitting operation tray portion 97a of an endoscope cover tray 97 can be opened and closed by a lid 97h, so that the inside of the fitting operation tray portion 97a can be always kept clean although the lid 97h and a holding portion 97i are contaminated.

Figure 48:
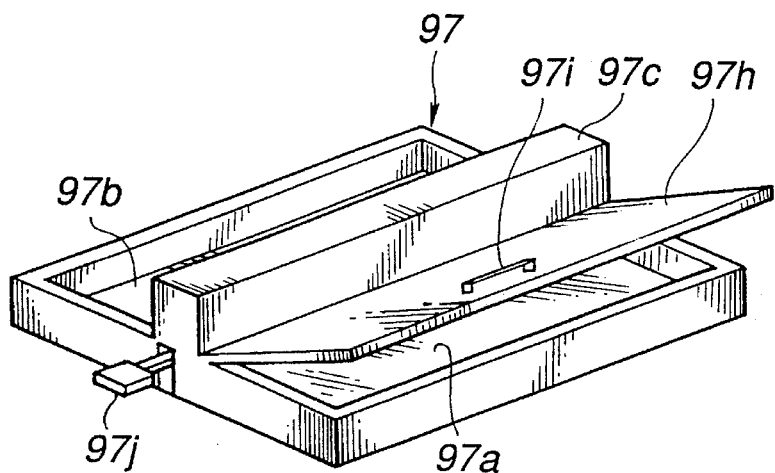
FIG. 48 is a perspective view of an endoscope cover tray in the 32nd embodiment of the present invention.

FIG. 48 shows the 32nd embodiment of the present invention.

As shown in this embodiment, if the lid 97h is opened and closed by means of a pedal 97j, the lid 97h can be opened and closed with one touch of the pedal and maneuverability is high. Further, the lid 97h is prevented from being contaminated because the lid 97h is opened and closed by means of the pedal 97j. When the pedal 97j is stepped on, the lid 97h is opened and when stepped off, it is closed. The opening and closing means may be electrically or mechanically operated.

Figure 49:
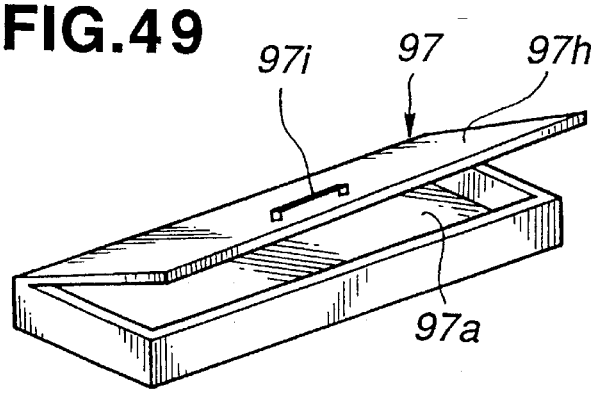
FIG. 49 is a perspective view of an endoscope cover tray in the 33rd embodiment of the present invention.

FIG. 49 shows the 33rd embodiment of the present invention.

As shown in this embodiment, the endoscope cover tray 97 may only contain a fitting operation tray 97a.

Figure 50:
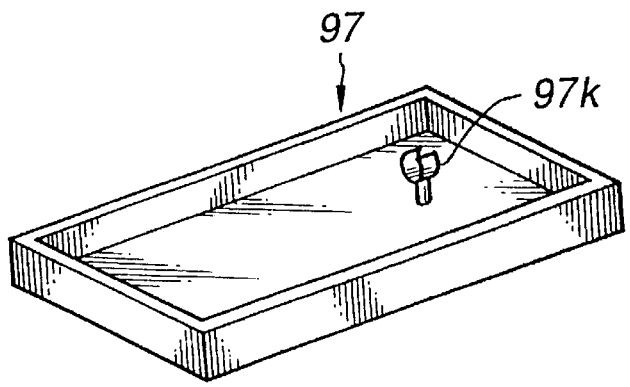
FIGS. 50 and 51 show the 34th embodiment of the present invention.
Figure 51:
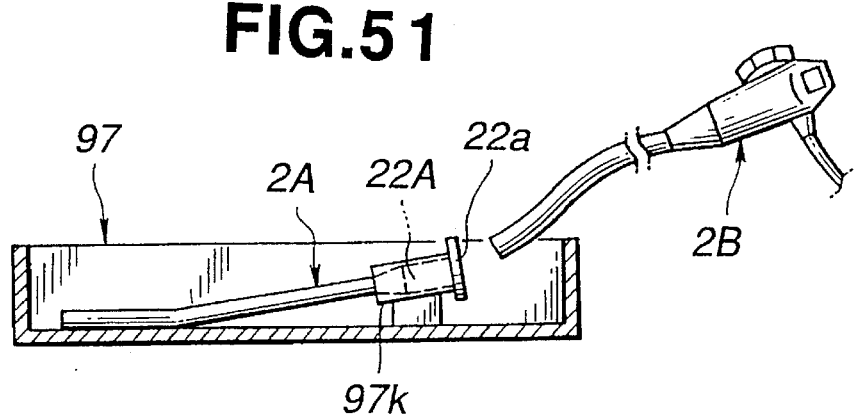

FIGS. 50 and 51 show the 34th embodiment of the present invention.

As shown in this embodiment, a cover holder 97k holding a connector for fixing an endoscope operation part 22A provided in a proximal portion of an endoscope cover 2A may be provided on the endoscope cover tray 97 shown in FIG. 42.

When the endoscope cover 2A covers an endoscope to be covered 2B, first, the endoscope cover 2A is inserted into the cover holder 97k. Then, a flange portion 22a provided in the connector for fixing an endoscope operation part 22A is caught by the cover holder 97k so that the connector for fixing an endoscope operation part 22A is held by the cover holder 97k.

Next, an endoscope to be covered 2B is inserted into the endoscope cover 2A. After the connector for fixing an endoscope operation part 22A is fixed to the endoscope to be covered 2B, the endoscope to be covered 2B is pulled out with the endoscope cover 2A.

Because the endoscope to be covered 2B can be covered without touching the endoscope cover 2A, maneuverability is high and the covered endoscope is clean.

Figure 52:
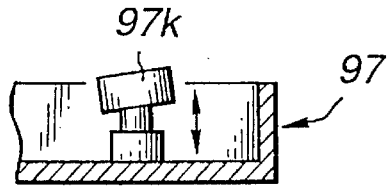
FIG. 52 is a sectional view of the essential part of an endoscope cover tray in the 35th embodiment of the present invention.

FIG. 52 shows the 35th embodiment of the present invention.

As shown in this embodiment, the cover holder 97k shown in FIGS. 50 and 51 may slide up and down. Because the cover holder 97k is slidable up and down, the cover holder 97k is slid up when an endoscope cover is fitted to an endoscope to be covered. Thus, by sliding the cover holder 97k up and down due to the slidable cover holder 97k, the interference with the lower surface of the endoscope cover tray 97 is prevented and then, the fitting operation can be smoothly performed. Further, the cover holder 97k is lowered so as not to be in the way when housed, therefore, is easily handled.

Figure 53:
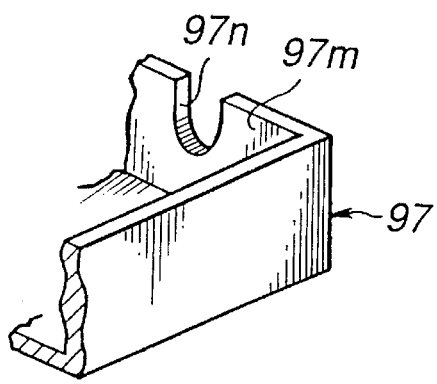
FIG. 53 is a sectional perspective view of the essential part of an endoscope cover tray in the 36th embodiment.

FIGS. 53 shows the 36th embodiment of the present invention.

As shown in this embodiment, a cover holding groove 97n is provided on a wall surface 97m of the endoscope cover tray 97 shown in FIG. 42, so that a connector for fixing an endoscope operation part 22A of an endoscope cover 2A is caught by the cover holding groove 97n by means of a flange portion 22a(see FIG. 51). Therefore, it is not necessary to especially provide the cover holder 97k shown in FIG. 51. Thus, the structure of the apparatus can be simple. Further, there is no obstacle, so that the apparatus can be easily handled.

In the present invention, it is apparent that working modes different in a wide range can be formed on the basis of the invention without departing from the spirit and scope of the invention. This invention is not restricted by its specific working mode except that it is limited by the appended claims.

What is claimed is:

1. A cover type endoscope apparatus comprising:

an endoscope cover; and an endoscope to be covered which is insertable into said endoscope cover, wherein an inner periphery of said endoscope cover includes a connector for fixing a fitting portion fitted to an engaging portion provided in an outer periphery of said endoscope to be covered, wherein said fitting portion holds and fixes at least one portion of said endoscope to be covered and wherein said connector includes a cover position adjusting means for adjusting the longitudinal axial position of said cover covering said endoscope to be covered.

2. The cover type endoscope apparatus according to claim 1, wherein said fitting portion is an elastic material.

3. The cover type endoscope apparatus according to claim 1, wherein a plurality of said fitting portions are provided on the inner periphery of said endoscope cover.

4. The cover type endoscope apparatus according to claim 1, wherein said connector for fixing an endoscope includes a first connector having said fitting portion, a second connector joined to a cover member covering an insertion tube of said endoscope to be covered, and wherein said cover position adjusting means includes a length controlling means for joining said first and second connectors, and wherein said length controlling means is a flexible and accordion-like tube.

5. The cover type endoscope apparatus according to claim 1, wherein said connector for fixing an endoscope includes:

a first connector having said fitting portion; and a second connector joined to a cover member covering an insertion tube of said endoscope to be covered, wherein said cover position adjusting means includes a length controlling means, provided in said first and second connectors, being slidable with each other, and wherein said engaging portion is engageable with said length controlling means at an arranged position.

\* \* \* \* \*